US007259140B2

(12) United States Patent
San Antonio et al.

(10) Patent No.: US 7,259,140 B2
(45) Date of Patent: Aug. 21, 2007

(54) HEPARIN-BINDING PEPTIDES AND USES THEREOF

(75) Inventors: James D. San Antonio, Media, PA (US); Barbara P. Schick, Merion Station, PA (US); Angela Verrecchio, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/551,005

(22) PCT Filed: Mar. 29, 2004

(86) PCT No.: PCT/US2004/009668

§ 371 (c)(1),
(2), (4) Date: Jan. 12, 2006

(87) PCT Pub. No.: WO2005/014619

PCT Pub. Date: Feb. 17, 2005

(65) Prior Publication Data

US 2006/0172931 A1    Aug. 3, 2006

Related U.S. Application Data

(60) Provisional application No. 60/458,241, filed on Mar. 28, 2003.

(51) Int. Cl.
*A61K 38/00* (2006.01)
(52) U.S. Cl. .......................................... 514/8; 530/324
(58) Field of Classification Search ..................... 514/8
See application file for complete search history.

(56) References Cited

U.S. PATENT DOCUMENTS

| | | | |
|---|---|---|---|
| 4,829,000 A | 5/1989 | Kleinman et al. | |
| 5,238,919 A | 8/1993 | Zimmerman et al. | |
| 5,332,671 A | 7/1994 | Ferrara et al. | |
| 5,380,716 A | 1/1995 | Conrad et al. | |
| 5,409,897 A | 4/1995 | Thomas et al. | |
| 5,464,815 A | 11/1995 | Chamow et al. | |
| 5,510,328 A | 4/1996 | Polarek et al. | |
| 5,556,836 A | 9/1996 | Roedern et al. | |
| 5,770,563 A | 6/1998 | Roberts et al. | |
| 5,849,689 A | 12/1998 | Chamow et al. | |
| 5,851,989 A | 12/1998 | Chamow et al. | |
| 5,877,153 A | 3/1999 | Harris et al. | |
| 5,968,822 A | 10/1999 | Pecker et al. | |
| 6,194,558 B1 | 2/2001 | Gianturco et al. | |
| 6,395,707 B1 | 5/2002 | Zioncheck et al. | |
| 6,855,801 B1 | 2/2005 | San Antonio et al. | 530/300 |
| 2003/0069170 A1 | 4/2003 | Soltero et al. | |

FOREIGN PATENT DOCUMENTS

| WO | WO95/13083 | 5/1995 |
|---|---|---|
| WO | WO97/47312 | 12/1997 |
| WO | WO 00/45831 | 8/2000 |

OTHER PUBLICATIONS

D.V. Sakharov et al., "Binding And Retention Of Polycationic Peptides And Dendrimers In The Vascular Wall", *FEBS Letters*, 537, 2003, pp. 6-10.
A. Lundequist et al., "Polycationic Peptides As Inhibitors Of Mast Cell Serine Proteases", *Biochemical Pharmacology*, 65, 2003, pp. 1171-1180.
E. Andersson et al., "Antimicrobial Activities Of Heparin-Binding Peptides", *Eur. J. Biochem*, 271, 2004, pp. 1219-1226.
A. Verrecchio et al., "Design Of Peptides With High Affinities For Heparin And Endothelial Cell Proteoglycans", *The Journal Of Biological Chemistry*, 275, 2000, pp. 7701-7707.
B. Schick et al., "Novel Concatameric Heparin-Binding Peptides Reserve Heparin And Low-Molecular-Weight Heparin Anticoagulant Activities In Patient Plasma In Vitro And In Rats In Vivo", *Blood*, 103, 2004, pp. 1356-1363.
S.C. Hodgkinson, "Glycosaminoglycan Binding Characteristics Of The Insulin-Like Growth Factor-Binding Proteins", *Journal Of Molecular Endocrinology*, 13, 1994, pp. 105-112.
A.G. Gibson, et al., "Orientation Of Heparin-Binging Sites In Native Vitronectin", *The Journal Of Biological Chemistry*, 274, 1999, pp. 6432-6442.
H. Conrad, "Heparin-Binding Proteins", Academic Press, pp. 192-196.

(Continued)

*Primary Examiner*—Cecilia J. Tsang
*Assistant Examiner*—Maury Audet
(74) *Attorney, Agent, or Firm*—Drinker Biddle & Reath LLP; Daniel A. Monaco

(57) ABSTRACT

Heparin-binding peptides are provided of the formula $R_1(X_1B_1B_2X_2B_3X_3Y_1R_2)R_nR_3$, $R_1(X_1B_1B_2B_3X_2X_3B_4X_4Y_1R_2)R_nR_3$, and $C(X_1B_1B_2B_3X_2X_3B_4X_4)_nC$; wherein $X_1$, $X_2$, $X_3$, and $X_4$ are independently selected from the group consisting of hydropathic amino acids; $B_1$, $B_2$, $B_3$, and $B_4$ are independently selected from the group consisting of basic amino acids; C is cysteine; $Y_1$ is zero or one to ten amino acid residues, wherein at least one amino acid residue is proline; n is an integer from one to ten; and $R_1$, $R_2$, and $R_3$ are independently selected segments containing from zero to twenty amino acid residues, provided, at least one of the segments $R_1$, $R_2$, and $R_3$ comprises at least one hydrophobic amino acid residue. The peptide $C(X_1B_1B_2B_3X_2X_3B_4X_4)_nC$ is optionally cyclized via a disulfide bond formed between cysteine residues. The peptides are administered to reduce plasma LMWH and heparin levels and to reduce the anticoagulant effects of heparin and LMWH. The peptides are also administered to inhibit microbial growth and to inhibit mast cell serine proteases involved in various diseases and disorders. The peptides are also administered as carriers to deliver active agents.

17 Claims, 11 Drawing Sheets

OTHER PUBLICATIONS

M.A. Pinhal, et al., "Heparin And A Cyclic Octaphenol-Octasulfonic Acid (GL-522-Y-1) Bind With High Affinity To A 47-KDA Protein From Vascular Endothelial Cell Surface And Stimulate The Synthesis And Structural Changes Of Heparan Sulfate Proteoglycan", *Thromb Res*, 103, 2001, pp. 35-45.

Z Mostafavi-Pour, et al., "Identification Of A Novel Heparin-Binding Site In The Alternatively Spliced IIICS Region Of Fibronectin: Roles Of Integrins And Proteoglycans In Cell Adhesion To Fibronectin Splice Variants", *Matrix Biol*, 20, 2001, pp. 63-73. Abstract Only.

J Kappler et al., "Glycosaminoglycan-Binding Propertie And Secondary Structure Of The C-Terminus Of Netrin-I", *Biochem Biophys Res Commun*, 271, 2000, pp. 287-291.

S.E. Sakiyama et al., "Incorporation Of Heparin-Binding Peptides Into Fibrin Gels Enhances Neurite Extension: An Example Of Designer Matrices In Tissue Engineering", *FASEB J.*, 13, 1999, pp. 2214-2224.

S. Liu et al., "A Peptide Sequence Of Heparin/Heparan Sulfate (HP/HS)-Interacting Protein Supports Selective, High Affinity Binding Of HP/HS And Cell Attachment", *Journal of Biol Chem*, 273, 1998, pp. 9718-9726.

F. Chillemi et al., "Synthesis And Cytotoxic Activity Of New Peptides Containing Basic Amino Acid Residues", *Anticancer Res.*, 18, 1998, pp. 757-758.

R.E. Hileman et al., "Glycosaminoglycan-Protein Interactions; Definition of Consensus Sites In Glycosaminoglycan Binding Proteins", *Bioessays*, 20, 1998, pp. 156-167.

J.R. Fromm et al., "Pattern And Spacing Of Basic Amino Acids In Heparin Binding Sites", *Arch Biochem Biophys* 343, 1997, pp. 92-100.

S. Liu et al., "A Heparin-Binding Synthetic Peptide Of Heparin/Heparan Sulfate-Interacting Protein Modulates Blood Coagulation Activities", *Proc. Natl. Acad. Sci.*, 94, 1997, pp. 1739-1744.

G.J. Taylor et al., "Glycosaminoglycan Specificity Of A Heparin-Binding Peptide", *Pept Res*, 1995, pp. 286-293.

W.A. Patton 2nd et al., "Identification Of A Heparin-Binding Protein Using Monoclonal Antibodies That Block Heparin Binding To Porcine Aortic Endothelial Cells", *Biochem J*, 311, 1995, pp. 461-469. Abstract Only.

K Mizuno et al., "Hairpin Loop And Second Kringle Domain Are Essential Sites For Heparin Binding And Biological Activity Of Hepatocyte Growth Factor", *J. Biol Chem*, 269, pp. 1131-1136.

T.W. Wakefield et al., "Reversal Of Low-Molecular-Weight Heparin Anticoagulation By Synthetic Protamine Analogues", *J. Surgical Research*, 56, 1994, pp. 586-593.

D.S. Ferran et al., "Design and Synthesis Of A Helix Heparin-Binding Peptide", *Biochemistry*, 31, 1992, pp. 5010-5016.

A.D. Cardin, "Molecular Modeling Of Protein-Glycosaminoglycan Interactions", *Arteriosclerosis*, 9, 1989, pp. 21-32.

B.R. Tomasini et al., "On The Identity Of Vitronectin And S-Protein: Immunological Crossreactivity And Functional Studies", *Blood*, 68, 3, 1986, pp. 737-742.

H. Margalit et al., "Comparative Analysis Of Structurally Defined Heparin Binding Sequences Reveals a Distinct Spatial Distribution Of Basic Residues", *The Journal Of Biological Chemistry*, 268, 1983, pp. 19228-19231.

H.C. deBoer, et al., "Binding Of Vitronectin-Thrombin-Antithrombin III Complex To Human Endothelial Cells Is Mediated By The Heparin Binding Site Of Vitronectin", *The Journal Of Biological Chemistry*, 267, 1982, pp. 2264-2268.

J.M. McPherson, et al., "The Effects of Heparin on the Physicochemical Properties of Reconstituted Collagen", *Collagen Rel. Res.*, 1:65-82 (1998).

L.H. Lam, et al., "The Separation of Active and Inactive Forms of Heparin", *Biochem. Biophys. Res. Comm.*, 69(2):570-577 (1976).

J.D. San Antonio, et al., "Heparin Sensitive and Resistant Vascular Smooth Muscle Cells: Biology and Role in Restenosis", *Connective Tissue Research*, 37(1-2):87-103.

J.S. San Antonio, et al., "Interactions of Syndecan-1 and Heparin with Human Collagens", *Glycobiology*, 4(3):327-332 (1994).

U. Lindahl, et al., "Glycosaminoglycans and Their Binding to Biological Macromolecules", *Ann. Rev. Biochem.*, 47:385-417 (1978).

J. Lawler, et al., "The Structure of Human Thrombospondin, and Adhesive Glycoprotein with Multiple Calcium-Binding Sites and Homologies with Several Different Proteins", *J. Cell. Biology*, 103:1635-1648 (1986).

E.C. Tsilibary, et al., "Heparin Type IV Collagen Interactions: Equilibrium Binding and Inhibition of Type IV Collagen Self-Assembly", *J. of Biological Chemistry*, 263(35): 19112-19118 (1988).

F.J. Bober Barkalow, et al., "Localization of the Major Heparin-Binding Site in Fibronectin", *J. Biological Chemistry*, 266(12):7812-7818 (1991).

R. L. Jackson, et al., "Glycosaminoglycans: Molecular Properties, Protein Interactions, and Role in Physiological Processes", *Physiological Reviews*, 71(2):481-539 (1991).

M.K. Lee, et al., "Analysis of Affinity and Structural Selectivity in the Binding of Proteins to Glycosaminoglycans: Development of a Sensitive Electrophoretic Approach", *Proc. Natl. Acad. Sci.*, 88:2768-2772 (1991).

J. Sandstrom, et al., "The Heparin-Binding Domain of Extracellular Superoxide Dismutase C and Formation of Variants with Reduced Heparin Affinity", *J. Biological Chemistry*, 267(25):18205-18209 (1992).

N. Guo, et al., "Heparin-Binding Peptides from the Type I Repeats of Thrombospondin", *Journal of Biological Chemistry*, 267(27):19349-19355 (1992).

M. Maccarana, et al. "Minimal Sequence in Heparin/Heparan Sulfate Required for Binding of Basic Fibroblast Growth Factor", *Journal of Biological Chemistry*, 268(32):23898-23905 (1993).

L.D. Thompson, et al., "Energetic Characterization of the Basic Fibroblast Growth Factor-Heparin Interaction: Identification of the Heparin Binding Domain", *Biochemistry*, 33:3831-3840 (1994).

N. Parthasarathy, et al., "Oligosaccharide Sequences of Endothelial Cell Surface Heparan Sulfate Proteoglycan with Affinity for Lipoprotein Lipase", *Journal of Biological Chemistry*, 269(35):22391-22396 (1994).

P. Wong, et al. "Analysis of Putative Heparin-Binding Domains of Fibroblast Growth Factor-1", *Journal of Biological Chemistry*, 270(43):25805-25811 (1995).

J.D. San Antonio, et al., "Mapping the Heparin-Binding Sites on Type 1 Collagen Monomers and Fibrils", *Journal of Cell Biology*, 125(5):1179-1188 (1994).

R. Matsumoto, et al., "Packing of Proteases and Proteoglycans in the Granules of Mast Cells and Other Hematopoietic Cells", *Journal of Biological Chemistry*, 270(33):19524-19531 (1995).

U. Lindahl, et al. "Regulated Diversity of Heparan Sulfate", *Journal of Biological Chemistry*, 273(39):24979-24982 (1998).

(ARKKAAKA)$_4$

[CYCL](ARKKAAKA)$_4$[CYCL]

(ARKKAAKA)$_3$(ARKKCAKA)

(ARKKAAKA)(A$_{16}$)(ARKKAAKA)

(ARKKAAKA)$_3$VLVLVLVL (AKKARA)$_6$

[PEPTIDE] (nM)

HEPARIN-BINDING PEPTIDES AND USES THEREOF

REFERENCE TO GOVERNMENT GRANT

This invention was supported in part using funds obtained from the U.S. Government (Department of the Army, Army Cooperative Agreement No. DAMD17-97-2-7016). The U.S. Government may therefore have certain rights in this invention.

FIELD OF THE INVENTION

The invention relates to heparin-binding peptides, compositions, and their use. More specifically, the invention relates to heparin-binding peptides with hydrophobic sequences which have higher heparin-neutralizing activities and potentially higher affinities for glycosaminoglycans and proteoglycans than heparin-binding peptides without hydrophobic sequences. The invention also relates to cyclized heparin-binding peptides.

BACKGROUND OF THE INVENTION

Heparin, a glycosaminoglycan, is a highly sulfated polyanionic polysaccharide composed of alternating residues of N-acetyl-glucosamine and glucuronic acid, and is the most widely used clinical anticoagulant. The major clinical applications for heparin include treatment of deep vein thrombosis (DVT) and thromboembolism (TE), prophylactic treatment of patients at high risk for DVT and TE from numerous medical conditions, post-operative prevention of DVT and TE, and prevention of clotting and thrombus formation resulting from interventions in the circulatory system. The circulatory system intervention procedures include cardiovascular diagnostic procedures, catheterization, surgery of the heart and vessels, and many other procedures including extracorporeal circulation, such as hemodialysis, use of artificial organs, and organ transplantation. However, once the procedure has been completed, in many cases the anticoagulation effects of heparin must be neutralized or reversed in order to prevent the patient from bleeding. Protamine is the only agent approved by the FDA for heparin reversal, and administration of protamine has a high incidence of adverse hemodynamic and anaphylactic events. Low molecular weight heparins (LMWH) are being used increasingly as a substitute for conventional unfractionated heparin (UFH) in thromboprophylaxis for numerous medical conditions and for post-surgical prophylaxis, e.g., following hip or knee replacement. Treatment of these patients with either UFH or LMWH results in significant incidence of serious bleeding. Protamine can neutralize the activity of UFH but is not effective in neutralizing LMWH in vivo.

The protamines, purified from fish sperm, are a family of basic proteins rich in arginine residues. Protamine appears to neutralize heparin's biologic effects by overwhelming the carbohydrate with cationic charges. Unfortunately, it may be toxic due to high charge density or distribution of charged residues and its administration frequently causes such problems as hypotension, pulmonary artery hypertension, myocardial depression, complement activation, thrombocytopenia, and leukopenia.

Glycosaminoglycans (GAG)s such as heparin also modulate enzyme activities (e.g., of antithrombin III or heparin cofactor II), regulate cell behavior (e.g., cell adhesion, growth, and differentiation), and control the function of extracellular matrices (e.g., diffusion of ions through basement membranes, and fibrillogenesis and lateral associations of collagens), largely through non-covalent interactions with proteins. (Jackson, R. L., et al., Physiol. Rev. 71:481-539, 1991; Lindahl, U. and M. Hook, Ann. Rev. Biochem. 47:385-417, 1978; San Antonio, et al., Connective Tissue Res., 37:87-103, 1998; WO00/45831). Although many proteins exhibit high affinity interactions with heparan sulfate, heparin, and other GAGs, the specificity of such interactions has been defined for only a small number of them. As heparan sulfates and heparin are among the most structurally diverse and biologically active GAGs, their protein-interactive features have been the most thoroughly studied.

A specific heparin pentasaccharide sequence is known to be an antithrombin III binding site. The site is a pentasaccharide composed of a 6-O-sulfated glucosamine in the first position, a 3-O-sulfated central glucosamine, two N-sulfated glucosamines, and a carboxylated iduronic acid. Other modifications may increase the activity of heparin on antithrombin III, but are not essential for activity.

Cardin and Weintraub identified two potential consensus sequence motifs for heparin-binding, X-B-B-X-B-X or X-B-B-B-X-X-B-X, where X represents a hydropathic or uncharged amino acid, and B a basic amino acid (Cardin, A. D. and H. J. R. Weintraub, Arteriosclerosis 9:21-32, 1989). For example, such consensus sequences were identified in proteins including apolipoprotein B-100, apo E, and vitronectin. Molecular modeling of these consensus sites predicts the arrangement of amino acids into either α-helices or β-strands. This allows for the clustering of noncontiguous basic amino acids on one side of the helix, thus forming a charged domain to which GAGs could bind. Indeed, for some heparin-binding proteins, disruption of the heparin-binding consensus sequences hinders heparin binding. For example, chemical modification of the heparin-binding consensus site in thrombospondin (Lawler, J. and R. O. Hynes, J. Cell Biol. 103:1635-1648, 1986) or site-directed mutagenesis of a heparin-binding sequence in fibronectin (FN) (Barkalow, F. J. B. and J. E. Schwarzbauer, J. Biol. Chem. 266:7812-7818, 1991) eliminates or diminishes heparin-binding affinity. On the other hand, peptide mimetics of proposed heparin binding consensus sequences often fail to reveal the high affinities demonstrated by the native heparin-binding proteins (Conrad, H. E, Heparin-Binding Proteins. Academic Press, 1998). Proteins often contain multiple, distal heparin-binding sequences that may come into proximity upon protein folding or multimerization, hence enabling binding through cooperativity.

The heparin-binding domain of von Willebrand factor resembles the motif XBBXXBBBXXBBX, a palindromic sequence in which the spacing and clustering of basic residues is important for heparin binding (Sobel, M., et al., J. Biol. Chem. 267:8857-8862, 1992). A third novel sequence has been demonstrated to be sufficient for weak heparin-binding in thrombospondin: WSXW (Guo, N. H., et al., J. Biol. Chem., 267:19349-19355, 1992). However, for high affinity binding, this sequence must be flanked by basic residues. Other proteins including type I collagen (Sweeney, S. M., et al., Proc. Natl. Acad. Sci. USA 95:7275-7280, 1998), extracellular-superoxide dismutase (Sandstrom, J., et al., J. Biol. Chem., 267:18205-18209, 1992), and mast cell chymases (Matsumoto, R., et al., J. Biol. Chem., 270:19524-19531, 1995), bind heparin via highly-basic binding regions which do not conform to any consensus sequence. In fact, in certain proteins, domains rich in basic amino acids have sometimes been shown to be unimportant for heparin binding. For example, the two heparin-binding consensus sequences identified in the FGFs were shown not to mediate heparin-binding (Wong, P., et al., J. Biol. Chem., 270:25805-25811, 1995; Thompson, L. D., et al., Biochem., 33:3831-3840, 1994).

GAG structure may also play a role in determining binding affinity and selectivity for proteins. A classic example is the antithrombin-binding site on heparin, which is present on only about one third of heparin chains (Lam, L. H., et al., Biochem. Biophys. Res. Commun., 69:570-577, 1976), but which has a thousand-fold greater affinity for antithrombin III than the overall heparin structure (Lee, M. K., and A. D. Lander, Proc. Natl. Acad. Sci. USA, 88:2768-2772, 1991). Several other sequences or structural motifs have been identified in GAGs which underlie their binding interactions with basic fibroblast growth factor (bFGF) (Maccarana, M., et al., J. Biol. Chem., 268:23898-23905, 1993), lipoprotein lipase (Parthasarathy, N., et al., J. Biol. Chem., 269:22391-22396, 1994), and interleukin-8 (Lindahl, U., et al., J. Biol. Chem., 273:24979-24982, 1998).

Other aspects of GAG structure also contribute to specific interactions with proteins. For example, heparin displays high affinities for sequences in short basic peptides with contiguous clusters of basic amino acids, whereas heparan sulfate displays high affinities for those sequences in which clusters of basic amino acids are separated by non-basic residues (Fromm, J. R., et al., Arch. Biochem. Biophys. 343 (1):92-100, 1997). Such binding preferences may relate to the increased spacing between highly sulfated domains found throughout heparan sulfate as compared with the more uniformly densely sulfated heparin. Heparin is capable of binding to a wide array of proteins, due to its high degree of flexibility.

There is a long felt need in the art for heparin-binding peptides which have greater affinity for heparin and a greater ability to neutralize heparin activity and LMWH activity and little or no hemodynamic toxicity compared to present heparin-binding peptides. The present invention satisfies these needs.

SUMMARY OF THE INVENTION

The compounds of the present invention are in the form of peptides which bind heparin and which possess heparin-neutralizing activity.

In all embodiments, the peptide may optionally comprise an amino terminal protecting group and/or a carboxy-terminal protecting group.

The heparin-binding peptides of the invention have the formula:

$R_1(X_1B_1B_2X_2B_3X_3Y_1R_2)_nR_3$ or $R_1(X_1B_1B_2B_3X_2X_3B_4X_4Y_1R_2)_nR_3$ wherein:

$X_1$, $X_2$, $X_3$, and $X_4$ are independently selected from the group consisting of hydropathic amino acids;

$B_1$, $B_2$, $B_3$, and $B_4$ are independently selected from the group consisting of basic amino acids;

$Y_1$ is independently (i) zero amino acid residues, or (ii) one to ten amino acid residues, wherein at least one of said amino acid residues is proline;

n is an integer from one to ten;

$R_1$, $R_2$, and $R_3$ are independently selected segments containing from zero to twenty amino acid residues, provided, at least one of the segments $R_1$, $R_2$, and $R_3$ comprises at least one hydrophobic amino acid residue.

The heparin-binding peptides of the invention contain the heparin-binding segment $X_1B_1B_2X_2B_3X_3Y_1R_2$ or the heparin-binding segment $X_1B_1B_2B_3X_2X_3B_4X_4Y_1R_2$. When the peptide of the invention contains more than one heparin-binding segment, i.e., n is greater than 1, the amino acid at position $X_1$ in one heparin-binding segment is selected independently of the amino acid at position $X_1$ in each other heparin-binding segment of the peptide. Similarly, the amino acid(s) selected for the $X_2$, $X_3$, $X_4$, $B_1$, $B_2$, $B_3$, $B_4$, $Y_1$, or $R_2$ positions of a heparin-binding segment are selected independently from the amino acids for the corresponding $X_2$, $X_3$, $X_4$, $B_1$, $B_2$, $B_3$, $B_4$, $Y_1$, or $R_2$ in each other heparin-binding segment of the peptide.

For example, when n is 2, the $Y_1$ in the N-terminal heparin-binding segment may be proline, and the $Y_1$ in the C-terminal heparin-binding segment may be zero amino acid residues. Two examples of such compounds are the peptides VLVLARKKAAARKKAAVLVL (SEQ ID NO:14) and VLVLAKKARAPAKKARAVLVL (SEQ ID NO:18). In each of these two peptides the $Y_1$ in the N-terminal heparin-binding segment is proline and the $Y_1$ in the C-terminal heparin-binding segment is zero amino acid residues.

In one embodiment of the invention, the heparin-binding segment ($X_1B_1B_2X_2B_3X_3Y_1R_2$) is the amino acid sequence AKKARA (SEQ ID NO:41) and the heparin binding segment ($X_1B_1B_2B_3X_2X_3B_4X_4Y_1R_2$) is the amino acid sequence ARKKAAKA (SEQ ID NO:29).

In one aspect, a heparin-binding peptide of the invention is selected from the group consisting of amino acid sequences SEQ ID NO:1, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:31, SEQ ID NO:32, SEQ ID NO:33, SEQ ID NO:34, SEQ ID NO:37, SEQ ID NO:38, SEQ ID NO:45, SEQ ID NO:46, and SEQ ID NO:47.

In one embodiment, the amino acids in the $X_1$, $X_2$, $X_3$, and $X_4$ positions are independently selected from the group consisting of alanine, asparagine, cysteine, glutamine, glycine, histidine, isoleucine, leucine, proline, serine, tyrosine, threonine, tryptophan, methionine, phenylalanine, and valine.

In one aspect of the invention, alanine, which stabilizes α-helical conformation, occupies at least one of the $X_1$, $X_2$, $X_3$, and $X_4$ hydropathic residue positions. In another aspect, $X_1$ is alanine. In yet another aspect, $X_1$, $X_2$, $X_3$ are alanine.

In one embodiment of the invention, at least one of $B_1$, $B_2$, $B_3$, and $B_4$ is arginine. In another aspect, $B_1$ is arginine.

In another embodiment of the invention, at least one of $B_1$, $B_2$, $B_3$, and $B_4$ is lysine. In one aspect, $B_1$ is lysine. In a further aspect of the invention, $B_2$ is lysine and $B_3$ is arginine.

In one embodiment of the invention, at least one of $B_1$, $B_2$, $B_3$, and $B_4$ is histidine.

In one aspect of the invention, n may be 1, 2, 3, 4, 5, 6, 7, 8, 9, or 10, representing the number of copies of the heparin-binding segment. In one aspect of the invention, n is from 2 to 8. Preferably, n is from 2 to 6.

In one embodiment of the invention, at least one of the segments $R_1$, $R_2$, or $R_3$, comprises at least one or more hydrophobic amino acids. Examples of such amino acids include valine, leucine, and isoleucine.

In one embodiment of the invention, at least one hydrophobic amino acid of $R_1$, $R_2$, and $R_3$ is selected from the group consisting of valine, leucine, isoleucine, alanine, proline, phenylalanine, tryptophan, and methionine. Preferably the hydrophobic amino acids are selected from the group consisting of valine, leucine, and isoleucine.

In one aspect, all of the amino acid residues of $R_1$, $R_2$, or $R_3$ are hydrophobic amino acids. Hydrophobic sequences or amino acids need not appear at the peptide termini, but may be present in various copy numbers and positions of the heparin-binding peptide. In another aspect of the invention, a hydrophobic amino acid residue or segment is at a terminus of the peptide.

In one embodiment of the invention, $R_1$, $R_2$, and $R_3$ are independently from each other 0, 1, 2, 3, 4, 5, 6, 7, 8, 9, 10, 11, 12, 13, 14, 15, 16, 17, 18, 19, or 20 amino acid residues in length, wherein at least one of $R_1$, $R_2$, and $R_3$ is at least one amino acid in length. Preferably, at least one of $R_1$, $R_2$, and $R_3$ is from 2 to 20 amino acid residues in length. More preferably, at least one of $R_1$, $R_2$, and $R_3$ is from 2 to 10 amino acid residues in length. Even more preferably, at least one of $R_1$, $R_2$, and $R_3$ is from 4 to 8 amino acid residues in length.

In one aspect, $R_1$, $R_2$, and $R_3$ have sequences independently selected from the group consisting of VLVL (SEQ ID NO:27), VLVLVL (SEQ ID NO:28), VLVLVLVL (SEQ ID NO:2), ILIL (SEQ ID NO:35), ILILIL (SEQ ID NO:36), ILILILIL (SEQ ID NO:3), VIVI (SEQ ID NO:39), VIVIVI (SEQ ID NO:40), VIVIVIVI (SEQ ID NO:4), LLLLLLLL (SEQ ID NO:42), VFVFVFVF (SEQ ID NO:43), and VLVLVLVLVL (SEQ ID NO:44), or any permutation of hydrophobic residues.

In another aspect, $R_2$ has the sequence CA or the sequence CADA (SEQ ID NO:26).

In one embodiment of the invention, the peptides comprise standard amino acids. In one aspect, the amino acids may be nonstandard amino acids. In another aspect, at least one of the amino acids is a D isomer. In yet another aspect, an amino acid of the invention may be a synthetic amino acid.

In one embodiment, a heparin-binding peptide of the invention binds to heparin with a dissociation constant, $K_d$, of 1000 nM or lower. Preferably, the $K_d$ is 500 nM or lower. More preferably, the $K_d$ is 200 nM or lower, and even more preferably, the $K_d$ is 100 nM or lower.

In one embodiment of the invention, the heparin-binding peptide neutralizes heparin activity by at least 10% compared to the heparin activity when no heparin-binding peptide is present. In another aspect, the heparin-binding peptide neutralizes heparin activity by at least 30%. In yet another aspect, the heparin-binding peptide neutralizes heparin activity by at least 50%. In a further aspect, the heparin-binding peptide neutralizes heparin activity by at least 70%. In a preferred embodiment, the heparin-binding peptide neutralizes heparin activity by at least 90%.

In one embodiment, a heparin-binding peptide of the invention may comprise a proline residue. In one aspect, $Y_1$ comprises at least one proline residue. In one aspect of the invention, a heparin-binding peptide comprising a proline residue is selected from the group consisting of amino acid sequences SEQ ID NO:14, SEQ ID NO:15, SEQ ID NO:16, SEQ ID NO:17, SEQ ID NO:18, SEQ ID NO:19, SEQ ID NO:20, and SEQ ID NO:21.

In one aspect, a peptide of the invention comprises at least about thirty amino acid residues. In another aspect, a peptide of the invention comprises less than about two hundred fifty amino acid residues.

According to a further embodiment, a heparin-binding peptide of the invention has the formula $C(X_1B_1B_2B_3X_2X_3B_4X_4)_nC$ wherein:

$X_1$, $X_2$, $X_3$, and $X_4$ are independently selected from the group consisting of hydropathic amino acids;

$B_1$, $B_2$, $B_3$, and $B_4$ are independently selected from the group consisting of basic amino acids;

C is cysteine;

n is an integer from one to about ten; and said peptide is optionally cyclized via a disulfide bond formed between said cysteine residues. In another aspect, the segment $X_1B_1B_2B_3X_2X_3B_4X_4$ has the amino acid sequence SEQ ID NO:29. In a further aspect, n is 4.

In one embodiment of the invention, the peptides of the formula $C(X_1B_1B_2B_3X_2X_3B_4X_4)_nC$ comprise standard amino acids. In one aspect, the amino acids may be nonstandard amino acids. In another aspect, at least one of the amino acids is a D isomer. In yet another aspect, an amino acid of the invention may be a synthetic amino acid.

In one embodiment, a heparin-binding peptide of the formula $C(X_1B_1B_2B_3X_2X_3B_4X_4)_nC$ binds to heparin with a dissociation constant, $K_d$, of 1000 nM or lower. Preferably, the $K_d$ is 500 nM or lower. More preferably, the $K_d$ is 200 nM or lower, and even more preferably, the $K_d$ is 100 nM or lower.

In one embodiment of the invention, a heparin-binding peptide of the formula $C(X_1B_1B_2B_3X_2X_3B_4X_4)_nC$ neutralizes heparin activity by at least 10% compared to the heparin activity when no heparin-binding peptide is present. In another aspect, the heparin-binding peptide neutralizes heparin activity by at least 30%. In yet another aspect, the heparin-binding peptide neutralizes heparin activity by at least 50%. In a further aspect, the heparin-binding peptide neutralizes heparin activity by at least 70%. In a preferred embodiment, the heparin-binding peptide neutralizes heparin activity by at least 90%.

The invention also contemplates a pharmaceutical composition comprising one or more heparin-binding peptides as described herein and a pharmaceutically-acceptable carrier.

In one embodiment, the invention is a method of reducing plasma heparin levels in a subject in need of such treatment, comprising administering to the subject a pharmaceutical composition comprising at least one heparin-binding peptide as described herein, in an amount effective to reduce plasma heparin levels in a subject. In one aspect, the subject is a human.

In another embodiment, the invention is a method of reducing the anticoagulant effects of a heparin in a subject, comprising administering to a subject a pharmaceutical composition comprising at least one heparin-binding peptide as described herein, in an amount effective to reduce the anticoagulant effects of heparin. In one aspect, the subject is a human.

In another embodiment, the invention is a conjugate comprising a heparin-binding peptide conjugated to at least one active agent as described herein.

In another embodiment, the invention is a method of delivering at least one active agent to a tissue or cell displaying high levels of GAGs or PGs, comprising administering to a subject a pharmaceutical composition comprising at least one heparin-binding peptide-active agent conjugate as described herein, wherein the conjugate binds to the GAGs or PGs and delivers the active agent to the tissue or cell.

In another embodiment, the invention is a method of treating a mast cell serine protease-associated disorder in a subject, comprising administering to a subject a pharmaceutical composition comprising at least one heparin-binding peptide as described herein, in an amount effective to treat the mast cell serine protease-associated disorder.

In another embodiment, the invention is a method of treating a microbial infection in a subject, comprising administering to a subject at least one heparin-binding peptide as described herein, in an amount effective to treat the infection. In one aspect, the peptide is administered topically.

In another embodiment, the invention is a conjugate comprising a heparin-binding peptide conjugated to at least one carrier molecule as described herein.

In another embodiment, the invention is a method of reducing the anticoagulant effects of a heparin in a subject, comprising administering to a subject a pharmaceutical composition comprising at least one heparin-binding peptide conjugated to a carrier molecule as described herein, in an amount effective to reduce the anticoagulant effects of heparin.

The invention is also directed to the use of the aforementioned heparin-binding peptides, in medicine. The invention is also directed to the use of the heparin-binding peptides, for preparation of a medicament for
 (i) reducing plasma heparin levels in a subject in need of such treatment, or
 (ii) reducing the anticoagulant effects of a heparin, or
 (iii) methods of treatment as a carrier to deliver therapeutic active agents, or
 (iv) reducing or inhibiting the effects of mast cell serine proteases, such as the pro-inflammatory effects of these proteases, or
 (v) reducing or inhibiting microbial growth and activity.

Other aspects and advantages of the present invention are described in the drawings and in the following detailed description of the preferred embodiments thereof.

ABBREVIATIONS AND SHORT FORMS

The following abbreviations and short forms are used in this specification.

"ACE" means affinity coelectrophoresis.
"ADP" means adenosine diphosphate.
"ATIII" means antithrombin III.
"CD" means circular dichroism.
"GAG" refers to glycosaminoglycans.
"IU" refers to International Unit.
"$K_d$" means dissociation constant.
"LMWH" means low molecular weight heparin which has been purified from unfractionated heparin, obtained through enzymatic and/or chemical digestion of unfractionated heparin, or obtained through chemical synthesis.
"PG" means proteoglycans.
"TFPI" means tissue factor pathway inhibitor.
"UFH" means unfractionated heparin.

DEFINITIONS

The articles "a" and "an" are used herein to refer to one or to more than one (i.e., to at least one) of the grammatical object of the article. By way of example, "an element" means one element or more than one element.

As used herein, each "amino acid" is represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |

-continued

| Full Name | Three-Letter Code | One-Letter Code |
|---|---|---|
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

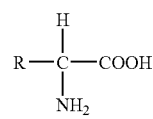

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

"Biologically active," as used herein with respect to heparin-binding peptides, means the ability of the peptide to bind to or neutralize or alter heparin activity as described herein. "Biologically active," as used herein with respect to heparin, means the ability of heparin to regulate cellular behaviors or to act as an anticoagulant. Various methods to assay these activities are described more fully in Examples 1 to 6.

The term "binding," as used herein, refers to the adherence of molecules to one another, such as, but not limited to, heparin-binding peptides to heparin, other glycosaminoglycans, or to proteoglycans.

An "effective amount" or "therapeutically effective amount" of a heparin-binding peptide, as used herein, is an amount sufficient to perform the functions described herein, such as neutralizing the anticoagulant activity of heparin, removing heparin from plasma, inhibiting microbial growth, inhibiting the effects mast cell serine proteases, or regulating the function of cells comprising cell surface heparin, other glycosaminoglycans, or proteoglycans, as in the promotion of the endothelialization of synthetic or naturally-derived vascular graft surfaces.

The term "glycosaminoglycan" refers to both heparin and non-heparin glycosaminoglycans. It is used interchangeably with "GAG."

The term "heparin activity" refers to the functions or properties of heparin, such as its ability to act as an anticoagulant. The term "heparin activity" is used interchangeably with "heparin function."

As used herein, "heparin-binding" refers to the ability of a molecule to bind with heparin, as determined by direct or indirect heparin-binding assays known in the art, such as the affinity coelectrophoresis (ACE) assay for peptide-glycosaminoglycan binding described in Example 1.

The term "heparin-binding peptide" or "heparin-binding segment" means a peptide or a sequence of amino acids within a peptide which binds with heparin, other glycosaminoglycans, or proteoglycans.

The term "hinge" refers to a flexible region of a peptide. "Hinge" is used interchangeably with "hinge region" herein.

"Hydropathic amino acid," as used herein, refers to an amino acid which is not hydrophilic in nature, i.e., it is not appreciably ionized at physiological or near physiological pH and salt concentrations.

The terms "hydrophobic segment," "hydrophobic sequence," or "hydrophobic domain," as used herein, refer to amino acid sequences containing amino acids which comprise nonpolar hydrophobic R groups at pH 6.0 to 7.0, such as the standard amino acids alanine, valine, leucine, isoleucine, proline, phenylalanine, tryptophan, and methionine.

The term "low molecular weight heparin" refers to heparins derived from unfractionated heparin, and which have a majority of their fragments in the 2000-6000 kD molecular weight range. It is used interchangeably with "LMWH."

"Neutralize heparin activity" means to inhibit or block a function of a heparin. The phrase refers to partial inhibition or blocking of a function, as well as to inhibiting or blocking most or all of a heparin activity.

As used herein, the terms "peptide" and "protein" are used interchangeably, and refer to a compound comprised of amino acid residues covalently linked by peptide bonds. A protein or peptide must contain at least two amino acids and no limitation is placed on the maximum number of amino acids which may comprise a protein's or peptide's sequence. The amino acids of the peptides described herein and in the appended claims are understood to be either D or L amino acids.

"Pharmaceutically acceptable" means physiologically tolerable, for either human or veterinary application.

As used herein, "pharmaceutical compositions" include formulations for human and veterinary use.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides, vol.* 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

A "segment" is a portion of an amino acid sequence, comprising at least one amino acid.

A "subject" of diagnosis or treatment is a mammal, including a human. Non-human animals subject to diagnosis or treatment include, for example, livestock and pets.

The term "unfractionated heparin," as used herein, refers to a type of heparin that is used clinically and has not been treated or subjected to purification to obtain low molecular weight heparin. The term is used interchangeably with "UFH."

The phrase "zipper," as used herein, refers to interaction between two or more peptides or to the regions of interaction. "Zipper" also refers to interaction of one region of a peptide with another region of the same peptide or to the regions of interaction of that peptide.

BRIEF DESCRIPTION OF THE FIGURES

FIG. 1A, (ARKKAAKA)$_4$ (SEQ ID NO:31); FIG. 1B, cyclized C(ARKKAA)$_4$C (SEQ ID NO:34); FIG. 1C, (ARKKAAKA)$_3$ (ARKKCAKA) (SEQ ID NO:33); FIG. 1D, (ARKKAAKA) (A$_{16}$)(ARKKAAKA) (SEQ ID NO:30); FIG. 1E, (ARKKAAKA)$_3$VLVLVLVL (SEQ ID NO:5); and FIG. 1F, (AKKARA)$_6$ (SEQ ID NO:32). FIGS. 1A to 1F represent phosphorimages of the gels. The concentration of peptide used is indicated below each lane and is expressed in nM concentrations. FIGS. 1G to 1L illustrate the corresponding computer analyses of the migration patterns of the radiolabeled heparin through different concentrations of peptide. The ordinate represents migration distance and "R" refers to the relative migration distance of the radiolabeled heparin from the loading well to the mid-point of sample migration. The abscissa represents peptide concentration expressed as nM. The calculated dissociation constant, $K_d$, for each peptide is also indicated on each graph.

DETAILED DESCRIPTION OF THE INVENTION

Figure 1A:
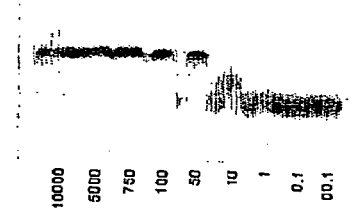
FIGS. 1A to 1L represent affinity coelectrophoresis (ACE) analyses of the binding of peptides of the invention to low molecular weight heparin as follows.
Figure 1B:
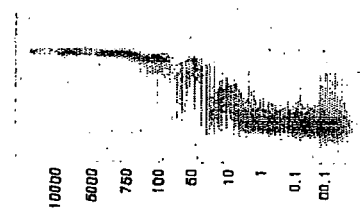
Figure 1C:
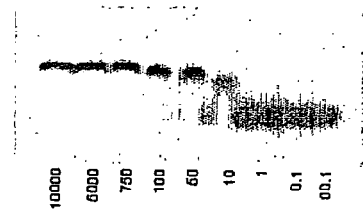
Figure 1D:
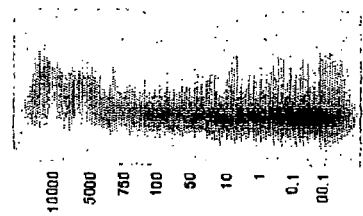
Figure 1E:
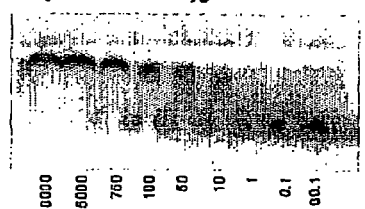
Figure 1F:
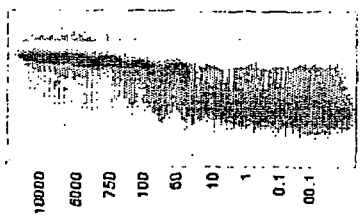
Figure 1G:
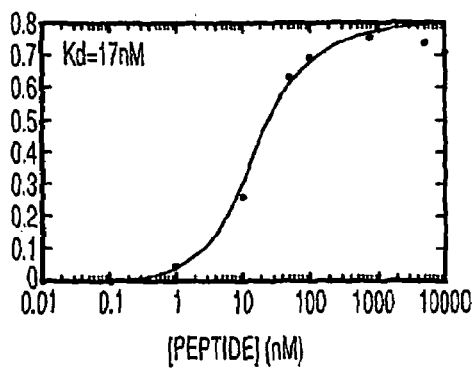
Figure 1J:
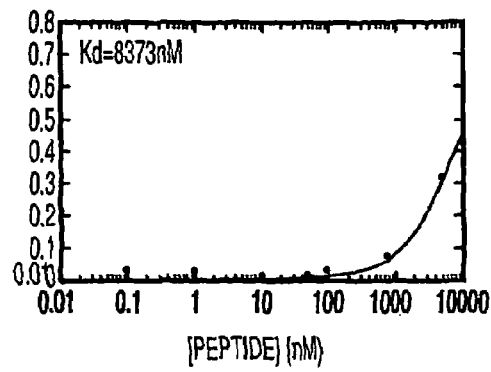
Figure 1H:
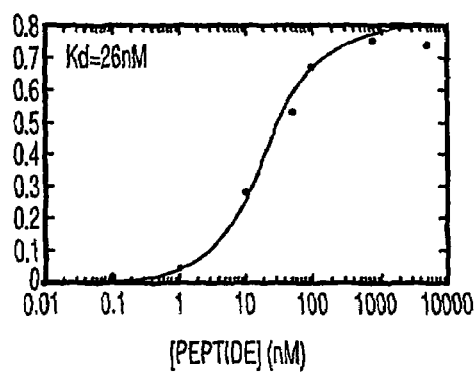
Figure 1K:
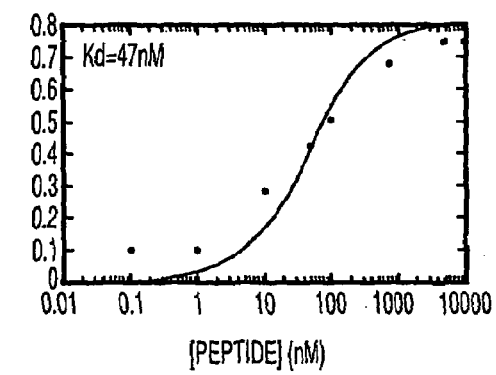
Figure 1I:
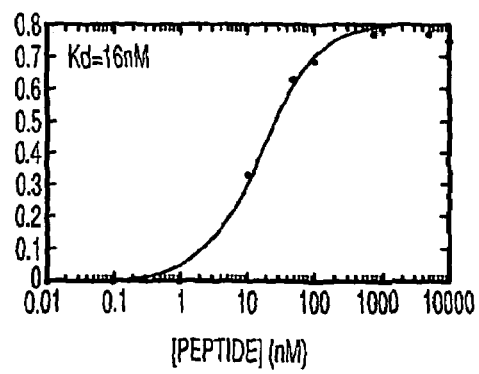
Figure 1L:
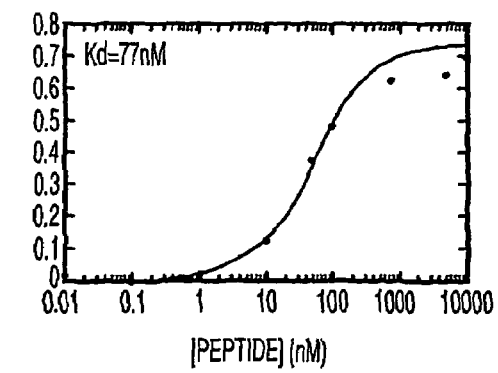
Figure 2A:
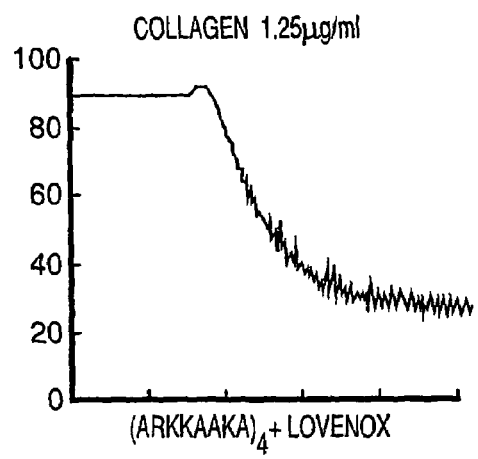
FIGS. 2A to 2E are tracings of the effect of two heparin-binding peptides of the invention on the aggregation of platelets in the presence of the aggregation-inducing agent collagen. The peptides tested were: (ARKKAAKA)$_4$ (SEQ ID NO:31) in FIG. 2A, (ARKKAAKA)$_3$(ARKKCAKA) (SEQ ID NO:33) in FIG. 2B, protamine in FIG. 2C, no peptide or low molecular weight heparin (control) in FIG. 2D, and the low molecular weight heparin enoxaparin sodium (Lovenox®, Aventis Pharmaceuticals, Inc.) alone in FIG. 2E. The ordinate (Y-axis) represents the inverse of % aggregation (90% is the initial setting). The abscissa (X-axis) represents time. Each tracing was taken for a period of 5 minutes.
Figure 2C:
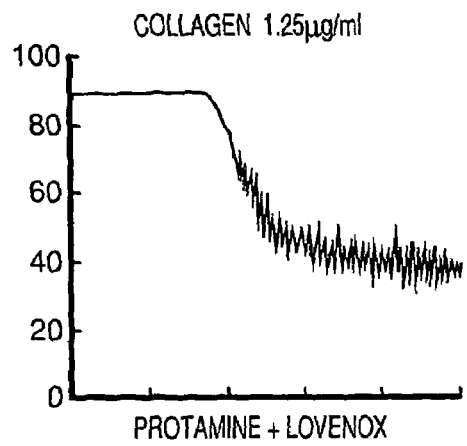
Figure 2B:
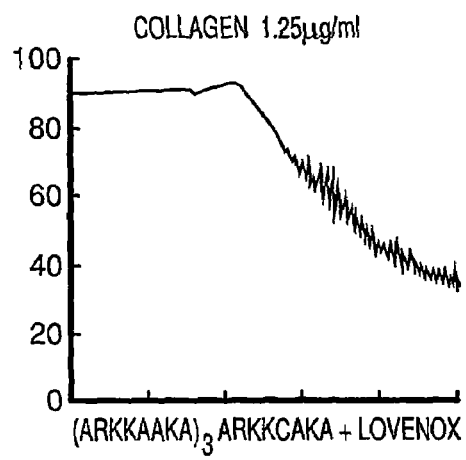
Figure 2D:
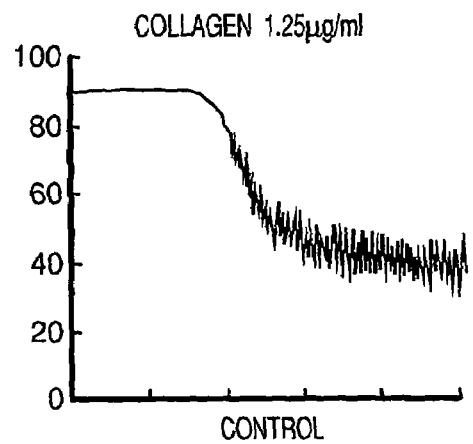
Figure 2E:
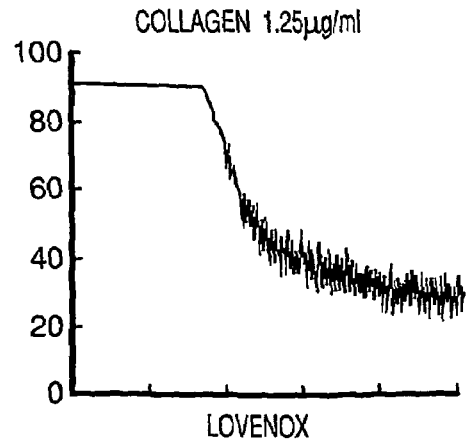

According to the present invention, unbranched heparin-binding peptides are provided which comprise hydrophobic segments. Cyclized heparin-binding peptides comprising at least two cysteine residues are also provided. The peptides may contain concatamers of heparin-binding consensus sequences that exhibit high affinity binding to low molecular weight heparin, other glycosaminoglycans, and endothelial cell proteoglycans. In one embodiment the peptides contain repeats of the heparin-binding amino acid sequences $X_1B_1B_2X_2B_3X_3Y_1R_2$ or $X_1B_1B_2B_3X_2X_3B_4X_4Y_1R_2$. The peptides have the formula $R_1(X_1B_1B_2X_2B_3X_3Y_1R_2)_nR_3$ or $R_1(X_1B_1B_2B_3X_2X_3B_4X_4Y_1R_2)_nR_3$. $X_1$, $X_2$, $X_3$, and $X_4$ are independently selected from the group consisting of hydropathic amino acids and $B_1$, $B_2$, $B_3$, and $B_4$ are independently selected from the group consisting of basic amino acids. $Y_1$ is: (i) zero amino acid residues, or (ii) one to ten amino acid residues, wherein at least one of the amino acid residues is proline. In addition, n is an integer from one to ten, $R_1$, $R_2$, and $R_3$ are independently selected segments containing from zero to twenty amino acid residues, provided, at least one of the segments $R_1$, $R_2$, and $R_3$ comprises at least one hydrophobic amino acid residue.

In addition, a heparin-binding peptide of the invention may comprise the formula $C(X_1B_1B_2B_3X_2X_3B_4X_4)_nC$. $X_1$, $X_2$, $X_3$, and $X_4$ are independently selected from the group consisting of hydropathic amino acids. $B_1$, $B_2$, $B_3$, and $B_4$ are independently selected from the group consisting of basic amino acids. C is cysteine, n is an integer from one to ten, and the peptide is optionally cyclized via a disulfide bond formed between said cysteine residues.

A heparin-binding peptide of the invention is one which possesses characteristics as described herein. For example, in one type of assay, a heparin-binding peptide exhibits detectable binding to low molecular weight heparin ($M_r$ less than 6 kDa) under the conditions of the affinity coelectrophoresis (ACE) assay for protein-glycosaminoglycan binding as described (in Example 1 below and San Antonio, J. D., and Lander, A. D., 2001, "Affinity coelectrophoresis of proteoglycan-protein complexes", in *Methods in Molecular Biology*, Vol. 171, *Proteoglycan Protocols*, pp. 401-414). In the ACE assay, binding is examined at approximately physiological conditions (pH 7.0, in the presence of 50 mM sodium 3-(N-morpholino)-2-hydroxypropanesulfonate (MOPSO)/125 mM sodium acetate) at 15° C., within a 1% agarose gel. Second, a heparin-binding peptide of the invention exhibits significant affinity for heparin. It is commonly considered that for native proteins, protein-heparin binding dissociation constants ($K_d$) in the range of 0.1-1000 nM are significant, and those higher than 1000 nM are negligible. Thus, a peptide of the invention that exhibits a heparin-binding affinity of 1000 nM or less is considered to be a "heparin-binding peptide." A heparin-binding peptide of the invention that exhibits an affinity of 100 nM or less is considered to be a high affinity heparin-binding peptide.

Hydropathic amino acids include the standard amino acids alanine, asparagine, cysteine, glutamine, glycine, histidine, isoleucine, leucine, proline, serine, tyrosine, threonine, tryptophan, methionine, phenylalanine, and valine. The invention includes the use of non-standard hydropathic amino acids as well. In contrast, amino acids that are appreciably ionized under physiological conditions are non-hydropathic, and include arginine, aspartic acid, lysine, and glutamic acid.

Hydrophobic amino acids which are contemplated by the invention include valine, leucine, isoleucine, alanine, proline, phenylalanine, tryptophan, and methionine. The invention includes all variants of such hydrophobic sequences with respect to residue number, amino acid composition, and arrangements.

The amino acid histidine contains the weakly basic imidazolium function and thus, can have the characteristics of both a basic amino acid and a hydropathic amino acid (Lehninger, in *Biochemistry*, Worth Publishers, Inc., Second edition, (1975), page 76). At pH 6.0, over half of histidine molecules possess a protonated, positively charged R group. However, at pH 7.0, less than ten percent of the molecules are positively charged. Thus, at pH 7.0 both charged and uncharged molecules are present, although most are uncharged, i.e., hydropathic. In addition, histidine is the only amino acid whose R group has a pK' near 7.0. Therefore, in one aspect of the invention histidine is a hydropathic amino acid. In another aspect of the invention, histidine is a basic amino acid.

The present invention should be construed to include, but should not be construed to be limited to, the following peptides herein after described, which are provided as non-limiting examples of the heparin-binding peptides of the invention.

The heparin-binding peptides of the invention may take the form of hydrophobic peptides with zipper regions comprising hydrophobic domains of various lengths. Hydrophobic domains can encourage conformation changes to better expose the binding domains of the peptide and can help increase solubility.

Such peptides include heparin-binding peptides with eight-amino acid hydrophobic segments such as ARKKAAKAARKKAAKAARKKAAKAVLVLVLVL (SEQ ID NO:5). The peptides of the invention also include heparin-binding peptides with six-amino acid hydrophobic segments such as AKKARAAKKARAAKKARAAKKARAAKKARAVLVLVL (SEQ ID NO:6) and ARKKAAKAARKKAAKAARKKAAKAVLVLVL (SEQ ID NO:7). The invention also includes heparin-binding peptides with ten-amino acid hydrophobic segments such as ARKKAAKAARKKAAKAARKKAAKAVLVLVLVLVL (SEQ ID NO:8). The invention also includes heparin-binding peptides with twelve-amino acid hydrophobic segments such as ARKKAAKAARKKAAKAARKKAAKAVLVLVLVLVLVL (SEQ ID NO:37). The peptides of the invention may also include peptides with limited numbers of heparin-binding sequences such as ARKKAAKAARKKAAKAVLVLVLVL (SEQ ID NO:9) and ARKKAAKAVLVLVLVL (SEQ ID NO:10).

The invention should be construed to include peptides with hydrophobic domains elsewhere in the peptide other than the termini, such as ARKKAAKAVLVLVLVLARKKAAKAARKKAAKA(SEQ ID NO:11) and ARKKAAKAARKKAAKAVLVLVLVLARKKAAKAARKKAAKA (SEQ ID NO:47).

The heparin-binding peptides of the invention include peptides with amino acids other than just valine and leucine in hydrophobic domains such as the peptide ARKKAAKAARKKAAKAARKKAAKAILILILIL (SEQ ID NO:12), in which the hydrophobic domain comprises isoleucine, but not valine, and the peptide ARKKAAKAARKKAAKAARKKAAKAVIVIVIVI (SEQ ID NO:13), in which the hydrophobic domain comprises isoleucine, but not leucine. Other peptides of the invention include ARKKAAKAARKKAAKAARKKAAKALLLLLLLL (SEQ ID NO:45), in which the hydrophobic domain comprises only leucines, and the peptide ARKKAAKAARKKAAKAARKKAAKAVFVFVFVF (SEQ ID NO:46), in which the hydrophobic domain comprises phenylalanine, but not leucine.

In another aspect of the invention, the heparin-binding peptides are synthesized to be conducive to hairpin or hinge conformation, by incorporating either cysteine or proline near one peptide terminus, with or without a hydrophobic segment at the other peptide terminus. Incorporation of these amino acids is conducive to flexibility and folding of the peptide. Flexibility and folding are important to form such structures as hairpins, loops, and hinges. Proline is involved in inducing hairpin turns and cysteine can promote dimerization or inter- or intra-chain covalent crosslinking, and either may be used to promote hinge formation within or between peptides. Without wishing to be bound by theory, basic residues on one or both ends of a peptide of the invention may bind/neutralize charges on the antithrombin-binding pentasaccharide sequence, and hydrophobic sequences (such as 2-, 4-, 6-, 8-, 10- or 12-mers) at the termini may promote association of the termini once the pentasaccharide is bound.

The heparin-binding peptides of the invention comprising proline, include, but are not limited to, the heparin binding-peptides VLVLARKKAAKAPARKKAAKAVLVL (SEQ ID NO:14), VLVLARKKAAKAPAAAAAAAAVLVL (SEQ ID NO: 15), VLVLARKKAAKAPARKKAAKADVLVL (SEQ ID NO:16), LVLARKKAAKAPAAAAAAAADVLVL (SEQ ID NO:17), VLVLAKKARAPAKKARAVLVL (SEQ ID NO: 18), VLVLAKKARAPAAAAAAVLVL (SEQ ID NO:19), VLVLAKKARAPAKKARADVLVL (SEQ ID NO:20), and VLVLAKKARAPAAAAAADVLVL (SEQ ID NO:21). Proline residues may be useful because they are usually encountered in loop, hairpin, hinge, or turn motifs and the cyclic nature of proline confers unique conformational properties to the peptide. Thus, two different peptides comprising proline residues may interact forming proline zippers or a peptide comprising a proline may fold such that intrapeptide interaction occurs.

Cysteine-containing heparin-binding domains of the invention include, but are not limited to, VLVLARKKAAKACA (SEQ ID NO:22), VLVLARKKAAKACADA (SEQ ID NO:23), VLVLAKKARACA (SEQ ID NO:24), VLVLAKKARACADA (SEQ ID NO:25), and VLVL(ARKKAAKA)$_3$ARKKCAKA (SEQ ID NO:38). A cysteine of a heparin-binding peptide of the invention may interact with a second cysteine of the same peptide, resulting in formation of a cyclized peptide from a linear sequence. Heparin-binding peptides of the invention also include dimers formed via cysteine-cysteine bonds between cysteine residues of two different peptides.

The peptides may also comprise D-isomeric forms wherein one or more of the amino acid residues are the D forms of the amino acid, and not the L form. Such D-isomeric peptides may comprise only D forms of amino acids. Peptides which include all D forms of amino acid residues, include, but are not limited to, the peptides ARKKAAKAARKKAAKAARKKAAKAARKKAAKA, AKKARAAKKARAAKKARAAKKARAAKKARA, and ARKKAAKAARKKAAKAARKKAAKAVLVLVLVL. D-isomers exhibit increased biological half-lives because they are not susceptible to plasma proteases, and it is believed that they bind to heparin equivalently to the natural L-form.

The peptides of the present invention are believed to have a number of uses. They are useful for neutralizing heparin activity, for reducing plasma heparin levels, for reducing the anticoagulant effects of heparin in a subject, and as heparin- and proteoglycan-binding modulators of hemostasis via interactions with endothelial cells. The peptides of the invention may also be used to promote cell adhesion, as in enhancing the endothelialization of synthetic or naturally-derived vascular graft surfaces, or to deliver active agents to cells and tissues rich in GAGs and proteoglycans compared to other cells and tissues, such as endothelial cells, connective tissue, and cartilage. In addition, the levels of GAGs and PGs may vary in cells or tissues subject to a disease or disorder.

Heparin activities include inhibition of smooth muscle cell proliferation, inhibition of clotting, and inhibition of Von Willebrand Factor. Heparin is used clinically to render blood incoagulable during open heart surgery, extracorporeal circulation, peripheral vascular surgery, organ transplantation, percutaneous angioplasty, and other acute vascular interventions. Heparin and LMWH are used clinically for the treatment of deep vein thrombosis and thromboembolism and as a prophylactic treatment for patients at high risk for DVT and thromboembolism. Such patients include but are not limited to individuals undergoing hip or knee replacement, pregnant women at risk for preeclampsia, cancer patients, and cardiac patients with ST segment elevation myocardial infarction.

The peptides of the present invention are useful for neutralization of unfractionated heparin, low molecular weight heparin, degradation products of heparin or LMWH, chemically synthesized and naturally occurring heparin pentasaccharide, or commercially available non-heparin glycosaminoglycan mixtures such as danaparoid sodium (Organan®, Organon, Inc., West Orange, N.J.; a mixture of chondroitin sulfate/heparan sulfate/dermatan sulfate). In humans, heparin is metabolized to the lower Mr fragments which contain the anticoagulant pentasaccharide fraction, which may remain in the circulation for extended periods of time, and for which no known antidote or neutralizing factor exists (see Examples 1-6).

The peptide (ARKKAAKA)$_3$VLVLVLVL (SEQ ID NO:5) and variants thereof described herein are shown to neutralize the low molecular weight heparin enoxaparin in the blood of low molecular weight heparin-treated human patients, whereas heparin-binding peptides lacking hydrophobic sequences may be less active or inactive (Example 1). Low molecular weight heparins (LMWH) are marketed in several pharmaceutically approved forms. These products are all derived from porcine unfractionated heparin by different proprietary chemical treatments, and generally have a majority of their fragments of Mr 2-6 kDa. Lovenox® is the trademark for the low molecular weight heparin product enoxaparin sold by Aventis Corp.

The heparin-binding peptides of the invention are useful to neutralize the anticoagulant activity of heparins without causing deleterious hemodynamic side effects. The peptides of the invention are also useful for reversing the anticoagulant activity of low molecular weight heparin in plasma in vitro, and thus are believed to have the ability to do so in humans in clinical settings.

The invention thus provides a method of treating diseases or conditions associated with heparin activity or treatment of a patient with heparin, comprising administering to a subject an amount of a heparin-binding peptide, or combination of heparin-binding peptides, or a combination of a heparin-binding peptide and another therapeutic agent, sufficient to diminish or neutralize the activity of heparin or to bind and remove heparin from the subject's circulatory system or locally. Without wishing to be bound by any particular theory, it is possible that mixtures of peptides may be needed to provide the most efficient neutralization of all forms of heparin. In preferred embodiments, the heparin-binding peptides are administered as pharmaceutically acceptable salts or a pharmaceutical composition.

The peptides of the present invention are useful agents for the promotion of cell-substratum attachment of proteoglycan (PG)-expressing cells (as in tissue engineering applications), and in the targeting of active agents to PG-expressing cells and PG-rich extracellular matrices, as in cartilage.

In another embodiment of the invention, the heparin-biding peptides are used by covalently attaching them to synthetic vascular grafts, to promote the attachment of endothelial cells comprising cell surface proteoglycans or glycosaminoglycans, thereby increasing the probability of graft success. Such grafts are useful to repair vascular damage due to disease or injury.

The peptides of the present invention have affinity for heparin/heparan sulfate on cell surfaces and potentially may be used as agents to promote wound-healing by dislodging antithrombin III (ATIII) and/or tissue factor pathway inhibitor (TFPI) from their binding sites and subsequently blocking these binding sites on the endothelium of broken blood vessels, thereby reducing the anticoagulant activity of the surface and enabling a clot to form.

The peptides of the present invention may be used to bind and neutralize or activate, or otherwise modulate the actions of various PGs or GAGs, thereby influencing their growth- or differentiation-modulating activities. For example, heparin and heparin-like molecules are known to inhibit smooth muscle cell proliferation, to potentiate the activities of growth factors like basic or acidic fibroblast growth factor on endothelial cells, and to inhibit or promote cell differentiation of smooth muscle cells, chondrocytes, and other cell types. The peptides described herein may be used to modulate the actions of heparin or endogenous heparan sulfate PGs, with significant consequences to cell growth and differentiation in normal, diseased, or injured tissue.

Heparin-binding peptides of the invention are useful as antimicrobial therapeutic agents, including, but not limited to, fungi and Gram-positive and Gram-negative bacteria. Microbes include, but are not limited to, microscopic organisms such as bacteria, fungi, protozoans, and viruses. In one aspect, heparin-binding peptides of the invention are bactericidal. In another aspect, the heparin-binding peptides are fungicidal.

In another embodiment, the heparin-binding peptides of the invention are useful for treating disorders and diseases involving or exacerbated by mast cell serine proteases such as chymase and tryptase. Diseases and disorders involving mast cell serine proteases include inflammatory responses, aberrant wound repair, rheumatoid arthritis, cancer, viral infection, bacterial infection, and allergic reactions such as bronchoconstriction and cutaneous reactions.

The peptides of the invention may be used as reagents for the affinity purification of bioactive sequences of GAGs. For example, some heparin-binding proteins have been shown to interact with specific sequences or domain structural features on heparins or heparan sulfates, including antithrombin III, lipoprotein lipase, and laminin. Thus, the peptides described herein are believed to exhibit binding preferences for distinct sequences in GAGs, making them useful as functional groups on affinity matrices for the purification of specific GAG sequences for a variety of uses.

The peptides of the invention can be used as vehicles or targeting agents to target "active agents" to cells and tissues displaying high levels of GAGs or PGs. An "active agent," as used herein, refers to a drug or compound which can be conjugated to a heparin-binding peptide of the invention where the heparin-binding peptide is used as a delivery vehicle or targeting agent. "Active agents" include "therapeutic agents" and "diagnostic agents." "Therapeutic agents" or "drugs" are those which have a beneficial effect on a specific disease or disorder in a living human or non-human animal. Therapeutic agents include, but are not limited to, drugs such as chemotherapeutic drugs and anti-inflammatory drugs. "Diagnostic agents" include compounds such as radionuclides or other molecules which can serve as reporter molecules in imaging or diagnostic tests.

For example, therapeutic and diagnostic agents conjugated to heparin-binding peptides can be targeted to cell surfaces of endothelial cell or other cell types which display specific targeted PGs or GAGs or to tissues or regions which display high concentrations of PGs or GAGs present on cell surfaces or in the extracellular matrix, such as the extracellular matrix of vascular tissue and the surfaces of endothelial cells lining the inner walls of blood vessels. As used herein, PGs and GAGs which are "displayed," or cells and tissues which "display high concentrations" of PGs and GAGs, refers to PGs and GAGs which are readily accessible for binding to a heparin-binding peptide of the invention. For example, PGs and GAGs which are on the surface of a cell or are in the extracellular matrix of connective tissue are generally accessible for binding to a heparin-binding peptide.

Active agents to be targeted to endothelial cells or other cell types may be conjugated with the peptides described herein, or the peptide sequences may be integrated into the active agent, and then the active agent is administered to the systemic circulation. The peptide component will mediate high affinity interactions with endothelial cell or other cell surfaces, as well as the extracellular matrix component of connective tissue, effectively delivering the active agent for action at that site, or potentially promoting the cellular uptake of the active agent.

In one aspect, a heparin-binding peptide of the invention is conjugated to at least one active agent. In another aspect, a heparin-binding peptide of the invention is conjugated to a first active agent and is also conjugated to a second different active agent. Peptides of the invention are useful in this context because they contain functional groups (e.g., amine or carboxyl groups of their constituent amino acids) to which active agents can be conjugated or linked. Such active agents include, for example, nucleic acids, radionuclides, other peptides, anti-inflammatory therapeutic agents (drugs), antibiotics, cytotoxic drugs such as chemotherapeutic agents, hormones, and polysaccharides. A cytotoxic drug is a therapeutic agent which is detrimental to the function of a cell or is lethal to a cell.

Conjugates of a heparin-binding peptide of the invention and an active agent can be formed by allowing the functional groups of the active agent and the peptide to form a linkage using coupling chemistries known to those of ordinary skill in the art. Numerous art-recognized methods for forming a covalent or other linkage can be used (see, e.g., March, J., Advanced Organic Chemistry, 4th Ed., New York, N.Y., Wiley and Sons, 1985, pages 326-1120). For example, a peptide of the invention can be conjugated to an active agent with bifunctional linkers or formation of biotin/streptavidin or biotin/avidin complexes by attaching either biotin or streptavidin/avidin to the peptide and the active agent to be delivered. Depending upon the nature of the reactive groups in the peptide of the invention and an active agent, a conjugate can be formed by simultaneously or sequentially allowing functional groups of the peptide and active agent to react with one another.

As used herein, "conjugated" means that two chemical moieties are joined by a chemical bond or by a linking moiety. Examples of chemical bonds include, covalent, hydrophilic, ionic, and hydrogen bonds. A preferred chemical bond is a covalent bond.

An active agent and a heparin-binding peptide of the invention may be conjugated directly or indirectly via a linker moiety. Direct conjugation may occur through any convenient functional group on the active agent such as a hydroxy, carboxy or amino group. Indirect conjugation occurs through a linking moiety. Suitable linking moieties include bi- and multi-functional alkyl, aryl, aralkyl or peptidic moieties, alkyl, aryl or aralkyl aldehydes acids esters and anyhdrides, sulhydryl or carboxyl groups, such as maleimido benzoic acid derivatives, maleimido proprionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups.

A linker moiety may also include a short sequence of from 1 to 4 amino acid residues that optionally includes a cysteine residue through which the linker moiety bonds to the peptide of the invention. In one aspect, the linker moiety is selected from (methylamino)benzoyl-Cys, succinimidobenzoyl-Cys, succinimidopropionoyl-Cys, β-alanyl-succinyl, acetyl-Cys and (4-aminoanilino)-succinimidopropionoyl-Cys. Disulfide linkages can be formed between thiol groups in, for example, the peptide of the invention and the active agent to be delivered. Alternatively, covalent linkages can be formed using bifunctional crosslinking agents, such as bismaleimidohexane (which contains thiol-reactive maleimide groups and which forms covalent bonds with free thiols). See also the Pierce Co. Immunotechnology Catalogue and Handbook Vol. 1 for a list of exemplary homo- and hetero-bifunctional crosslinking agents, thiol-containing amines and other molecules with reactive groups.

In a manner identical to the inclusion of a cysteine residue into a linker moiety, further amino acid residues may be included in the linker. For example, 3 or 4 amino acid residues may be included and these may include the cysteine residue discussed above. Any amino acid residues may be included.

Other methods for covalently coupling a heparin-binding peptide of the invention to a linking moiety and/or to an active agent include, for example, techniques using glutaraldehyde (Riechlin, Meth. Enzymology 70:159-165, 1980), N-ethyl-N'-(3-dimethylaminopropyl)-carbodiimide (Goodfriend et al., Science 144:1344-1346, 1964) and a mixture of N-ethyl-N'-(3-dimethylaminopropyl)-carbodiimide and a succinylated carrier (Klapper and Klotz, Meth. Enzymol. 25:531-536, 1972). Reactive functional groups that are present in the amino acids of the peptide may be protected, to minimize unwanted side reactions prior to coupling the peptide to a linking moiety and/or to an active agent.

In one aspect, the linker groups are incorporated site-specifically at a position which does not affect the specific binding properties of the heparin-binding peptide. In another aspect of the invention, a covalent bond between a peptide of the invention and an active agent is selected to be sufficiently labile (e.g., to enzymatic cleavage by an enzyme present in the targeted tissue) so that it is cleaved following transport of the active agent, thereby releasing the free active agent. Exemplary labile linkages are described in Low et al., U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

In one aspect, the active agent may be attached to either end of a heparin-binding peptide of the invention, e.g., the active agent may be attached to the terminal amino acid residue or to the terminal carboxy amino acid residue.

In another embodiment of the invention, a heparin-binding peptide of the invention is complexed with or conjugated to more than one active agent moiety. Each active agent moiety may be the same or different. When more than one type of active agent moiety is conjugated to a heparin-binding peptide of the invention, it is possible to co-ordinate the ratios and dosages of the individual active agents to facilitate the administration of specific active agent combinations.

Once prepared, heparin-binding peptide-active agent conjugates of the invention are tested to ensure that the heparin-binding peptide component of the conjugate has maintained its biological properties, such as heparin-binding, proteoglycan binding, and heparin neutralization.

The peptides of the present invention may be synthesized de novo using conventional solid phase synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroactetic acid (TFA), HCl in dioxane, boron tris-(trifluoracetate) and cyanogen bromide; and reaction in solution with isolation and purification of intermediates are methods well-known to those of ordinary skill in the art.

A preferred peptide synthesis method follows conventional Merrifield solid phase procedures well known to those skilled in the art. Additional information about solid phase synthesis procedures can be had by reference to Steward and Young, *Solid Phase Peptide Synthesis*, W.H. Freeman & Co., San Francisco, 1969; the review chapter by Merrifield in *Advances in Enzymology* 32:221-296, F. F. Nold, Ed., Interscience Publishers, New York, 1969; and Erickson and Merrifield, *The Proteins* 2:61-64 (1990), the entire disclosures of which are incorporated herein by reference. Crude peptide preparations resulting from solid phase syntheses may be purified by methods well known in the art, such as preparative HPLC. The amino-terminus may be protected according to the methods described for example by Yang et al., *FEBS Lett.* 272:61-64 (1990), the entire disclosure of which is herein incorporated by reference.

Peptides of the invention can be prepared by other techniques known to those of skill in the art, and include for example, standard recombinant nucleic acid techniques and chemical synthetic techniques.

The compounds of the invention may be natural or synthetic peptides produced by any known means, including synthesis by biological systems and chemical methods. Biological synthesis of peptides is well known in the art, and includes the transcription and translation of a synthetic nucleic acid encoding a heparin-binding peptide or biologically active fragments thereof. Chemical peptide synthesis includes manual and automated techniques well known to those skilled in the art. For example, automated synthesis can be performed with commercially available peptide synthesizers. Biologically active fragments according to the invention may also be obtained by the digestion or fragmentation of larger natural or synthetic peptides. Techniques to synthesize or otherwise obtain peptides and peptide fragments are well known in the art.

Alternatively, the heparin-biding peptides of the invention may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art.

General methods for the cloning and expression of recombinant molecules are described in Maniatis (Molecular Cloning, Cold Spring Harbor Laboratories, 1982), and in Sambrook (Molecular Cloning, Cold Spring Harbor Laboratories, Second Ed., 1989), and in Ausubel (Current Protocols in Molecular Biology, Wiley and Sons, 1987), which are incorporated by reference.

The nucleic acids encoding heparin-binding peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lac, T3, T7, lambda Pr'P1' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include, but are not limited to, SV40 polyadenylation signals and LTR polyadenylation signals.

The heparin-binding peptides prepared by either chemical synthesis or recombinant DNA technology may then be assayed for biological activity according to the assay methods described herein, as well as by methods known to those of skill in the art.

The heparin-binding peptides of the invention may be modified with other substances. The modifying substance may be joined to the heparin-binding peptide, for example, by chemical means (e.g., by covalent bond, electrostatic interaction, Van der Waals forces, hydrogen bond, ionic bond, chelation, and the like) or by physical entrapment. For example, the compounds of the invention may be modified with a label (e.g., substances which are magnetic resonance active; radiodense; fluorescent; radioactive; detectable by ultrasound; detectable by visible, infrared or ultraviolet light). Suitable labels include, for example, fluorescein isothiocyanate, peptide chromophores such as phycoerythrin or phycocyanin and the like; bioluminescent peptides such as the luciferases originating from *Photinus pyrali*; or fluorescent proteins originating from *Renilla reniformi*.

The compounds of the invention may also be modified with polymeric and macromolecular structures (e.g., liposomes, zeolites, dendrimers, magnetic particles, and metallic beads) or targeting groups (e.g., signal peptide sequences, ligands, lectins, or antibodies). Peptides or peptide fragments may further be modified with end protecting groups at the carboxyl or amino-terminal ends, amino-acid side chain modifying groups, and the like.

Modification of the heparin-binding peptides may alter their activity, for example by altering characteristics such as in vivo tissue partitioning, peptide degradation rate, heparin binding or heparin specificity. The modifications may also confer additional characteristics to the compound, such as the ability to be detected, manipulated or targeted.

Methods of modifying the heparin-biding peptides with other substances, in particular labels, are well known to those skilled in the art. For example, methods of conjugating fluorescent compounds such as fluorescein isothiocyanate to a peptide are described in Danen et al., Exp. Cell Res., 238:188-86 (1998), the entire disclosure of which is incorporated herein by reference. Methods of radiolabeling peptides with $^{125}I$ are disclosed by Sambrook et al. in *Molecular Cloning: A Laboratory Manual*, Cold Spring Harbor Laboratories, Second Ed., (1989), the disclosure of which is incorporated herein by reference.

In one aspect of the invention, the heparin-binding peptides may contain aspartic acid (D) residues to promote their solubility after neutralization of charges by complex formation.

In another embodiment of the invention, peptide longevity is enhanced by the addition of adducts such as sucrose or polyethylene glycol, production of peptide-IgG chimeras, or the peptides can be cyclized via cysteine-cysteine linkages, which is a modification known to enhance the biological activities of a variety of peptides.

In one aspect of the invention, a polyethylene glycol adduct is (2-aminoethyl)-O'-(N-diglycolyl-2-aminoethyl)-hexaethyleneglycol. In another aspect, a polyethylene glycol adduct is in the form of GK[(2-aminoethyl)-O'-(N-diglycolyl-2-aminoethyl)-hexaethyleneglycol]GG. The dipeptide GK increases peptide solubility. The dipeptide GG is present as a spacer between the solid support and peptide chain to improve the ease of peptide synthesis.

The invention also contemplates that any of the peptides may be derivatized with functional groups and/or linked to other molecules to facilitate their delivery to specific sites of action, to potentiate their activity, or complexed covalently or non-covalently to other pharmaceuticals, bioactive agents, or other molecules. Such derivatizations must be accomplished so as to not significantly interfere with the heparin- or PG-interactive properties of the peptides. Derivatizations must be designed or chosen so as not to exert toxic or undesirable activities on animals or humans treated with these formulations. Functional groups which may be attached to the peptides may include, but not be limited to, amines, alcohols, or ethers. Functional groups which may be covalently linked to the peptides to increase their in vivo half-lives may include, but not be limited to, polyethylene glycols, small carbohydrates such as sucrose, or peptides and proteins. The peptides may also be synthesized by recombinant DNA techniques with expression vectors for use in biological systems, such as bacteria, yeast, insect, or mammalian cells.

In one aspect, the peptides of the invention are conjugated to "carrier molecules" such as polymers to facilitate local delivery of the peptides to wound or surgical sites and to maintain the conjugated peptide at the site of administration. Molecules such as polymers which are conjugated to heparin-binding peptides of the invention to help facilitate delivery of the peptides are referred to as "carrier molecules" herein. Polymers which are useful as carrier molecules include for example, collagen, agarose and hyaluronic acid.

Polymers useful as carrier molecules of heparin-binding peptides are available linked to matrices such as surgical sheets or mats, or in suspensions for direct application to a wound or surgical site as a wound packing material or slurry. Techniques are also available for conjugating polymers to be used as carrier molecules to surgical sheets or mats. Carrier molecules attached to matrices are also useful in maintaining the conjugated peptide at the site of administration.

Heparin-binding peptides of the invention may be conjugated to carrier molecules by methods known in the art. A peptide of the invention and a carrier molecule may be conjugated directly or indirectly via a linker moiety. Direct conjugation may occur through any convenient functional group such as a hydroxy, carboxy or amino group. In one aspect, conjugation is via a covalent bond. In one aspect, the carrier molecule may be attached to either end of a heparin-binding peptide of the invention, e.g., the carrier molecule may be attached to the terminal amino acid residue or to the terminal carboxy amino acid residue of the peptide. More detailed methods for conjugating heparin-binding peptides of the invention to other molecules are provided above with respect to conjugating heparin-binding peptides to active agents.

Techniques such as NMR spectroscopy and measurement of incorporation of radiolabeled heparin-binding peptides of the invention onto polymers are used to quantify conjugation of a carrier to a heparin-binding peptide.

Generally, the amount of peptide administered depends upon the intended use of the peptide, such as the degree of heparin inhibition that is desired in a patient subjected to heparin therapy, or the extent and type of microbial infection being treated, or the amount of mast cell serine protease activity that must be inhibited during an allergenic reaction. Generally, the amount of peptide-active agent conjugate to be administered depends on the type of active agent being delivered, the tissue or cell being targeted, and the intended use of the active agent. Those skilled in the art may derive appropriate dosages and schedules of administration to suit the specific circumstances and needs of the patient. For example, suitable doses of heparin-binding peptide to be administered may be estimated from the amount of heparin or non-heparin glycosaminoglycan which had been administered to a patient. Typically, dosages of heparin-binding peptide are between about 0.001 mg/kg and about 100 mg/kg body weight. In some embodiments dosages are between about 0.01 mg/kg and about 60 mg/kg body weight. In other embodiments, dosages are between about 0.05 mg/kg and about 5 mg/kg body weight. Doses may also be estimated to be equivalent in potency to the dose of protamine which is currently used for heparin neutralization.

In general, the schedule or timing of administration of a heparin-binding peptide or heparin-binding peptide-active agent conjugate of the invention is according to the accepted practice for the procedure being performed. For example, during heart surgery, a peptide of the invention may be administered when the cardiopulmonary bypass pump is turned off, or shortly thereafter, where heparin neutralized is required. If bleeding occurs, additional heparin-binding peptide may be administered by titrating the dose to the heparin level as needed. Where heparin, or low LMWH, is administered for use in such procedures as thromboprophylaxis or treatment of thrombosis, and bleeding complications arise, a peptide of the invention may be administered slowly by single intravenous injection. If bleeding continues, a second smaller dose of peptide may be administered as a slow infusion within several hours of the first dosage. A peptide of the invention may also be administered locally at a site of bleeding. Local administration includes topical administration. Topical administration refers to administration to a surface, such as the skin.

When used in vivo, the peptides or peptide-conjugates of the invention are preferably administered as a pharmaceutical composition. The invention thus provides pharmaceutical compositions comprising a heparin-binding peptide, or a pharmaceutically acceptable salt thereof, and a pharmaceutically acceptable carrier. The heparin-binding peptide of the invention may be present in a pharmaceutical composition in an amount from 0.001 to 99.9 wt %, and more preferably from about 0.1 to 99.0 wt %. To achieve good plasma concentrations, a heparin-binding peptide or a combination of heparin-binding peptides, may be administered, for example, by intravenous injection, as a solution comprising 0.1 to 1.0% of the active agent.

The compositions of the present invention may comprise at least one active heparin-binding peptide or heparin-binding peptide-active agent conjugate, one or more acceptable carriers, and optionally other heparin-binding peptides or active agents.

For in vivo applications, the peptides or peptide-active agent conjugates of the present invention may comprise a pharmaceutically acceptable salt. Suitable acids which are capable of forming such salts with the compounds of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents or adjuvants. The compositions are preferably sterile and non-pyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g. 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the present invention can be prepared in a manner fully within the skill of the art.

The heparin-binding peptides of the invention, or heparin-binding peptide-active agent conjugates of the invention, or pharmaceutically acceptable salts thereof, or pharmaceutical compositions comprising these compounds, may be administered by any method designed to expose heparin-containing plasma or cell surface or extracellular matrix heparin/heparan sulfates of a subject to the compounds, so that the compounds may have a physiological effect. Administration may occur locally, enterally or parenterally; for example locally (e.g., with powders, ointments, lotions, creams, gels, pastes or drops), topically, orally, rectally, intracisternally, intravaginally, intraperitoneally, or as a buccal or nasal spray or aerosol. The route(s) of administration will be readily apparent to the skilled artisan and will depend upon any number of factors, including the type and severity of the condition or disease to be treated, the amount of heparin present, the age of the subject being treated, etc. Parenteral administration is preferred to reduce plasma heparin levels. Particularly preferred parenteral administration methods include intravascular administration (e.g. intravenous bolus injection, intravenous infusion, intra-arterial bolus injection, intra-arterial infusion and catheter instillation into the vasculature), peri- and intra-target tissue injection (e.g. peri-tumoral and intra-tumoral injection), subcutaneous injection or deposition including subcutaneous infusion (such as by osmotic pumps), intramuscular injection, and direct application to the target area, for example by a catheter or other placement device. For example, if a subject is being treated after heparin therapy, the heparin-binding peptides may be administered by intra-arterial or intra-venous infusion at the site of catheterization. Bleeding at the site of catheterization may be treated by direct or topical administration of heparin-binding peptides of the invention.

Where the administration of the heparin-binding peptide or of the heparin-binding peptide-active agent conjugate is by injection or direct application, the injection or direct application may be in a single dose or in multiple doses. Where the administration is by infusion, the infusion may be a single sustained dose over a prolonged period of time or multiple infusions.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLE 1

Analysis of Heparin-Binding Activity

Peptide Synthesis. Peptides were synthesized and purified using standard techniques as previously described (WO00/

45831). Peptides were synthesized by standard solid phase synthesis using FMOC chemistry. Peptide molecular weight was verified by mass spectroscopy, and purity (>70%) analyzed by HPLC.

Peptide-heparin interactions. The following heparin-binding peptides were synthesized: (ARKKAAKA)$_4$VLVLV-LVL (SEQ ID NO:1); (ARKKAAKA)$_4$ (SEQ ID NO:31); cyclized C(ARKKAAKA)$_4$C (SEQ ID NO:34); (ARKKAAKA)$_3$(ARKKCAKA) (SEQ ID NO:33); (ARKKAAKA)(Al$_6$)(ARKKAAKA) (SEQ ID NO:30); (ARKKAAKA)$_3$VLVLVLVL (SEQ ID NO:5); ARKKAAKAARKKAAKAARKKAAKAVLVLVL (SEQ ID NO:7); VLVLARKKAAKAPARKKAAKAVLVL (SEQ ID NO:14); (AKKARA)$_6$ (SEQ ID NO:32); and VLVL (ARKKAAKA)$_3$ARKKCAKA (SEQ ID NO:38).

Thus, a collection of peptides containing various consensus sequence motifs as described herein, as well as various modifications, was synthesized.

Preparation of Radiolabeled Heparin. Whole heparin from pig intestinal mucosa (Sigma) was tyramine end-labeled and radiolabeled with Na$^{125}$I (Amersham, Pharmacia Biotech, Inc., Piscataway, N.J.) to an average specific activity≅1.0× 10$^7$ CPM/µg as described (San Antonio, J. D., et al., Biochemistry, 32:4746-4755, 1993). Radiolabeled heparin was fractionated on Sephadex G-100 (Bio-Rad Laboratories, Hercules, Calif.) and the final≅12% of material to elute was retained as the low M$_r$ material of ≦6,000 (Jordan, R., D. Beeler, and R. Rosenberg, *J. Biol. Chem.*, 254:2902-2913, 1979; Laurent, T. C., et al., *Biochem. J.*, 175:691-701, 1978).

Analysis of Peptide-Heparin Interactions by Affinity Coelectrophoresis (ACE). ACE was used to study interactions between peptides and low molecular weight (low M$_r$) heparin (WO00/45831). In ACE, trace concentrations of radiolabeled heparin are electrophoresed through agarose lanes containing peptides at various concentrations. These analyses are used to determine the dissociation constants (K$_d$'s). The electrophoretic patterns of radiolabeled heparin are then visualized using a phosphorimager, and the dissociation constant (K$_d$) corresponds to the protein concentration at which the heparin is half shifted from being fully mobile at very low protein concentrations to maximally retarded at saturating protein concentrations. The lower the K$_d$ value, the higher the affinity.

Binding of radiolabeled heparin to peptides was studied by ACE as detailed elsewhere (San Antonio, J. D., et al., Biochemistry, 32:4746-4755, 1993). The heparin-protein binding affinities revealed by ACE match reasonably well with those obtained by other well established quantitative techniques for measuring binding interactions, e.g., (Lee, M. K., and A. D. Lander, Proc. Natl. Acad. Sci. USA, 88:2768-2772, 1991; McPherson, J. M., et al., Collagen Rel. Res., 1:65-82, 1988; San Antonio, J. D., et al, Biochemistry, 32:4746-4755, 1993; San Antonio, J. D., et al., J. Cell Biol., 125:1179-1188, 1994; San Antonio, J. D., et al., Glycobiol., 4:327-332, 1994; Tsilibary, E. C., et al., J. Biol. Chem., 263:19112-19118, 1988). Briefly, peptides were dissolved in 1×ACE running buffer, 50 mM sodium 3-(N-morpholino)-2-hydroxypropanesulfonate (MOPSO, Sigma)/125 mM sodium acetate, pH 7.0, and serially diluted in running buffer at 2× concentrations. Peptides were then mixed 1:1 with 2% agarose/1% CHAPS, 3-[(3-cholamidopropyl)dimethylammonio]-1-propanesulfonate, (Boehringer Mannheim, Indianapolis, Ind.), and loaded into wells of a 1% agarose gel. Radiolabeled heparin was then loaded in a slot on the anode side of the gel, and electrophoresed through the peptide-containing wells, towards the cathode. Gels were dried and PG mobility was measured with a Phosphorimager (Molecular Dynamics, Sunnyvale, Calif.) by scanning each protein lane and determining the relative radioactivity content per 88-µm pixel through the length of the lane. Retardation coefficient (R) measurements, binding isotherm curve fittings, and apparent K$_d$ value determinations were calculated as detailed previously (Lee, M. K., and A. D. Lander, Proc. Natl. Acad. Sci. USA, 88:2768-2772, 1991; San Antonio, J. D., et al, Biochemistry, 32:4746-4755, 1993).

Figures 1, 3:
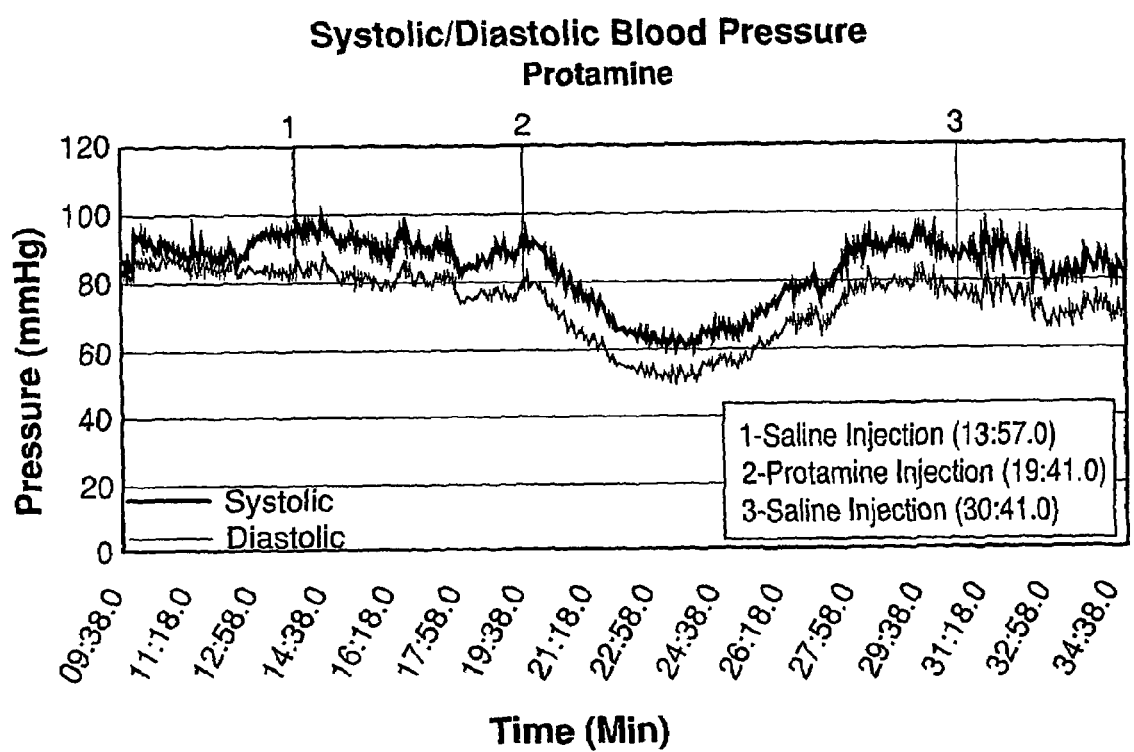
FIGS. 3-1 to 3-7 show the effects of heparin-binding peptides of the invention on blood pressure in rats. The following actions were taken at the times labeled on the graphs as 1, 2, 3, 4, or 5 and as further indicated by the box insert in each figure: administration of saline to insure that the animal and intubations were stable; administration of test peptide or protamine alone; then administration of protamine or saline. The animals were administered the following: protamine (FIG. 3-1), (ARKKAAKA)$_4$ (SEQ ID NO:31) (FIG. 3-2), ARKKAAKA(A)$_{16}$ARKKAAKA (SEQ ID NO:30) (FIG. 3-3), (ARKKAAKA)$_3$VLVLVLVL (SEQ ID NO:5) (FIG. 3-4), (ARKKAAKA)$_3$ARKKCAKA (SEQ ID NO:33) (FIG. 3-5), cyclized C(ARKKAAKA)$_4$C (SEQ ID NO:34) (FIG. 3-6), and (AKKARA)$_6$ (SEQ ID NO:32) (FIG. 3-7). The ordinate represents blood pressure (mmHg) and the abscissa represents time in minutes.
Figures 2, 3:
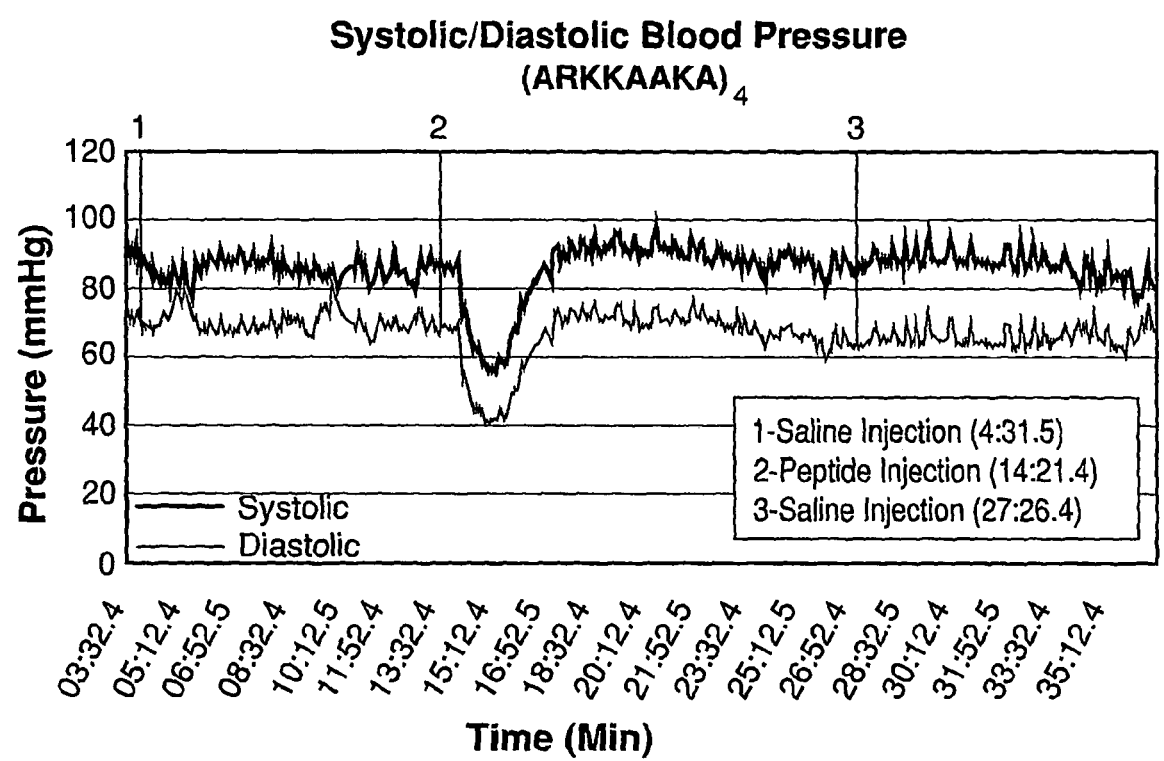
Figure 3:
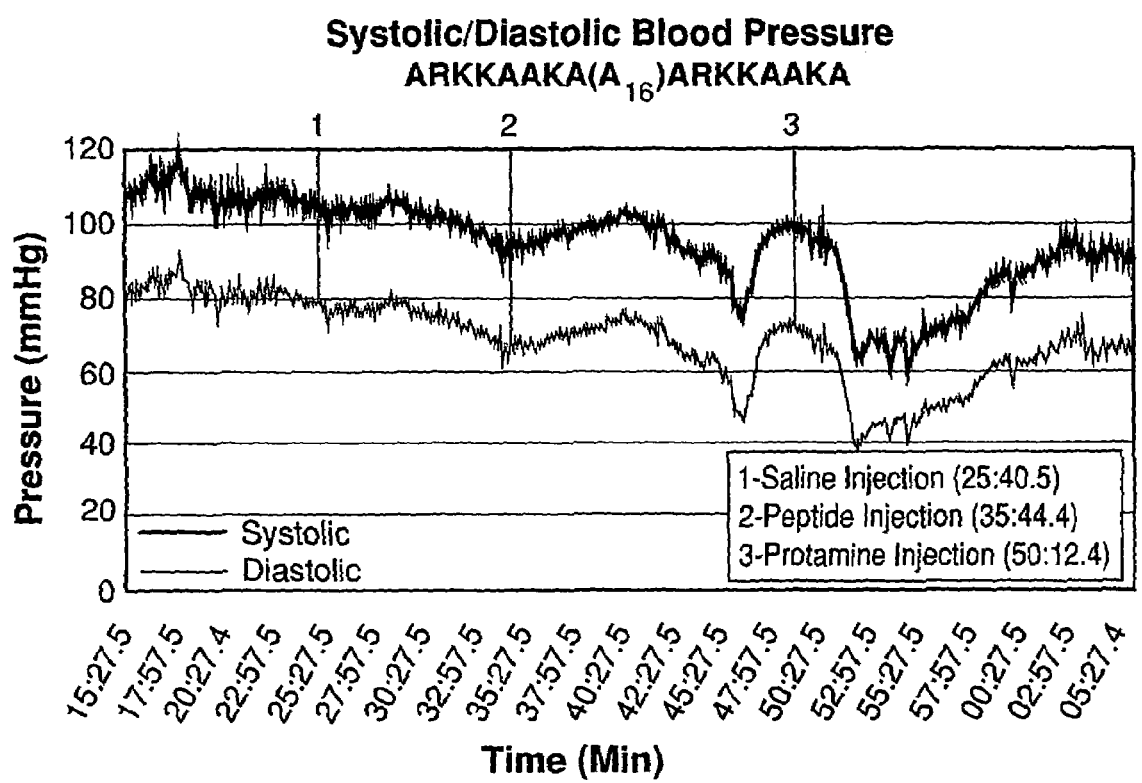

Retardation coefficients (R) for the migration of low Mr $^{125}$I-tyramine-heparin through peptides were determined from ACE gel electrophoretograms, and are plotted against peptide concentration. Smooth curves represent non-linear least-squares fits to the equation R=R∞/{1+(Kd/[peptide])$^n$}. Representative tracings are shown in FIG. 1.

A "heparin-binding peptide" may be classified as one which shows detectable binding to heparin or to low molecular weight heparin (M$_r$<6 kDa) under the conditions of the ACE assay for protein-glycosaminoglycan binding described in Example 1 below and also described by San Antonio, J. D., and Lander, A. D. (2001, *Methods in Molecular Biology*, Vol. 171, Proteoglycan Protocols, pp. 401-414). Under these conditions, a peptide that exhibits a heparin-binding affinity dissociation constant of 1000 nM or lower is considered to be a heparin-binding peptide.

Results. The ability of representative peptides of the invention to interact with heparins is illustrated in Table 1 and FIG. 1. The K$_d$'s listed in Table 1 were derived from four independent experiments and each number represents the mean and standard deviation of four independent assays. Representative gels from these assays are shown in FIG. 1. The monomer ARKKAAKA (SEQ ID NO:29) had negligible affinity for low molecular weight heparin. The concatamers of SEQ ID NOS:31-33 exhibited high affinity for low molecular weight heparin, as did the heparin-binding peptide of SEQ ID NO:1 comprising a concatamer and a hydrophobic segment. The cyclized heparin-binding peptide of SEQ ID NO:31 also exhibited high heparin affinity.

TABLE 1

Affinities of peptides for low molecular weight heparin.

| PEPTIDE | | K$_d$ (nM) |
|---|---|---|
| ARKKAAKA(A$_{16}$)ARKKAAKA | (SEQ ID NO:30) | 8327 ± 60 nM |
| (ARKKAAKA)$_4$ | (SEQ ID NO:31) | 55 ± 32 nM |
| (AKKARA)$_6$ | (SEQ ID NO:32) | 58 ± 16 nM |
| (ARKKAAKA)$_3$ARKKCAKA | (SEQ ID NO:33) | 54 ± 34 nM |

TABLE 1-continued

Affinities of peptides for low molecular weight heparin.

| PEPTIDE | | $K_d$ (nM) |
|---|---|---|
| (ARKKAAKA)$_3$VLVLVLVL | (SEQ ID NO:5) | 57 ± 23 nM |
| Cys-(ARKKAAKA)$_4$-Cys-Cyclized | (SEQ ID NO:34) | 38 ± 13 nM |
| (ARKKAAKA)$_3$VLVLVL | (SEQ ID NO:7) | 44 ± 17 nM |
| VLVL(ARKKAAKA)$_3$ARKKCAKA | (SEQ ID NO:38) | 48 ± 11 nM |
| VLVLARKKAAKAPARKKAAKAVLVL | (SEQ ID NO:14) | 5225 ± 1548 nM |

In summary, this example presents data demonstrating that representative peptides of the invention exhibit high affinity binding to LMWH.

EXAMPLE 2

Neutralizing Heparin Activity

Neutralizing Heparin Activity In Vitro: Effects of Peptides on the Anti-FACTOR Xa Assays in Citrate and in Control Plasma Containing UFH, LMWH or Orgaran®

The peptides having the sequences of SEQ ID NOs:1, 5, 7, 14, 30-34, and 38 were synthesized as described in Example 1.

The ability of peptides such as (ARKKAAKA)$_3$VLVLVL (SEQ ID NO:5) to neutralize the anti-Factor Xa activity of UFH and LMWH in vitro was tested using the Stachrom Heparin kit (Diagnostica Stago), a standard hematology laboratory assay used to measure the anti-Factor Xa activity of heparin. The assay was performed using the low molecular weight heparin enoxaparin sodium (Lovenox®, Aventis Pharmaceuticals, Inc.), unfractionated heparin (UFH), or the non-heparin glycosaminoglycan danaparoid sodium (Orgaran®, Organon Inc., West Orange, N.J.) in 0.32% citrate or in plasma anticoagulated with 0.32% citrate. Enoxaparin is commonly used clinically as a low molecular weight heparin (LMWH). Danaparoid is commonly used clinically as a non-heparin glycosaminoglycan anticoagulant. Currently, the only FDA approved drug to target UFH is protamine, which is not effective in vivo against LMWH or a non-heparin glycosaminoglycan such as danaparoid. Buffer and ATIII are added to form the heparin/ATIII complex, peptide is added, then Factor Xa, reporter dye substrate for Factor Xa activity, and stop solution, and the dye concentration is read at 405 nm. The absorbance of the dye increases with increasing Factor Xa activity, and thus is inversely proportional to the heparin (anti-Factor Xa activity) concentration. Peptides were tested in plasma obtained from three volunteers (A, B, and C). Platelet function inhibitors PG12 and theophylline were added to the blood immediately upon collection.

Results. The results are summarized in Tables 2A (Lovenox®), 2B (heparin), and 2C (Orgaran®. The tables indicate the concentrations of peptide (µg/l) relative to the volume of citrate or plasma used for the assay, and the amount of anti-Factor Xa activity neutralized (U/ml) by that concentration of peptide. In Table 2A, enoxaparin (Lovenox®) was present in each citrate or plasma sample at 0.7 U anti-Factor Xa activity/ml. For Table 2B, UFH was present in each citrate or plasma sample at 0.7 U anti-Factor XA activity/ml. The results in all three volunteers were virtually identical. As expected, the control peptide ARKKAAKA (SEQ ID NO:29) had no effect and the control peptide ARKKAAKA(A$_{16}$)ARKKAAKA (SEQ ID NO:30) had minimal effects in the anti-Factor Xa assay in both citrate and in plasma both for Lovenox® and UFH. Table 2A shows that Protamine, (ARKKAAKA)$_4$ (SEQ ID NO:31), (AKKARA)$_6$ (SEQ ID NO:32), C(ARKKAAKA)$_4$C (SEQ ID NO:34), (ARKKAAKA)$_3$VLVLVL (SEQ ID NO:7), and VLVL(ARKKAAKA)$_3$ARKKCAKA (SEQ ID NO:38) each had a greater anti-LMWH effect in citrate than in plasma. In contrast, (ARKKAAKA)$_3$VLVLVLVL was able to neutralize the same amount of Lovenox® in citrate and plasma. (ARKKAAKA)$_4$ (SEQ ID NO:31), (ARKKAAKA)$_3$ARKKCAKA (SEQ ID NO:33), (ARKKAAKA)$_3$VLVLVL (SEQ ID NO:5), and VLVL(ARKKAAKA)$_3$ARKKCAKA (SEQ ID NO:38) had similar effects to each other and were more effective than protamine at low concentrations in the presence of plasma. (ARKKAAKA)$_3$VLVLVL (SEQ ID NO:5) and VLVL(ARKKAAKA)$_3$ARKKCAKA (SEQ ID NO:38) were the most effective neutralizing agents. (ARKKAAKA)$_3$VLVLVLVL (SEQ ID NO:5) and VLVL(ARKKAAKA)$_3$ARKKCAKA (SEQ ID NO:38) were able to neutralize about 0.4 U/ml anti-Factor Xa activity of LMWH at a concentration of 12 µg/ml, which would be an effective dose for patients. (AKKARA)$_6$ (SEQ ID NO:31), (ARKKAAKA)$_4$ (SEQ ID NO:31) and (ARKKAAKA)$_3$ARKKCAKA (SEQ ID NO:38), neutralized 0.3-0.35 U/ml. In contrast, 12 µg protamine only neutralized about 0.25 U/ml of LMWH under these conditions.

Table 2B shows the data for UFH. Maximal activity was reached at 6 µg/ml. The peptides at 6 µg/ml neutralized at least 0.55 U/ml of anti-Factor Xa activity of UFH, while protamine only neutralized about 0.4 U/ml. (ARKKAAKA)$_3$ VLVLVLVL (SEQ ID NO:5) was again the most effective peptide. Table 3C shows that neutralization of non-heparin glycosaminoglycan Orgaran® at these peptide concentrations was only about 0.1 U/ml. Thus, the peptides of the invention exhibited similar potencies. Even though in all cases cited above a plateau was reached after which increasing concentrations of a single peptide had little effect, other data have demonstrated that some specific peptide combinations produced additive effects.

In summary, peptides of the invention which show high affinity for binding to LMWH, such as (ARKKAAKA)$_3$VLVLVLVL (SEQ ID NO:5), C(ARKKAAKA)$_4$C (SEQ ID NO:34), (ARKKAAKA)$_3$ARKKCAKA (SEQ ID NO:33), and (AKKARA)$_6$ (SEQ ID NO:32), have the ability to function well as neutralizers of LMWH and UFH in the anti-Factor Xa assay in plasma. All high-affinity peptides tested were better than protamine in the in vitro reversal of LMWH and UFH activity.

TABLE 2A

Effect of Peptides on anti-Factor Xa Activity of the Low Molecular Weight Heparin Lovenox ®

| | Lovenox ® Neutralized, U/ml | | | |
|---|---|---|---|---|
| μg/ml Peptide | Citrate | A Plasma | B Plasma | C Plasma |
| Protamine | | | | |
| 1 | 0.050 ± 0.016 | 0.038 ± 0.036 | 0.086 ± 0.004 | 0.070 ± 0.050 |
| 6 | 0.256 ± 0.060 | 0.177 ± 0.033 | 0.200 ± 0.026 | 0.232 ± 0.065 |
| 12 | 0.591 ± 0.032 | 0.232 ± 0.067 | 0.249 ± 0.039 | 0.285 ± 0.041 |
| 60 | 0.570 ± 0.033 | 0.515 ± 0.066 | 0.574 ± 0.022 | 0.465 ± 0.021 |
| 120 | 0.480 ± 0.058 | 0.562 ± 0.035 | 0.592 ± 0.037 | 0.499 ± 0.16 |
| (ARKKAAKA)$_4$ | | | | |
| 1 | 0.141 ± 0.051 | 0.020 ± 0.016 | 0.031 ± 0.015 | 0.059 ± 0.029 |
| 6 | 0.376 ± 0.019 | 0.184 ± 0.038 | 0.178 ± 0.022 | 0.252 ± 0.024 |
| 12 | 0.473 ± 0.039 | 0.287 ± 0.058 | 0.328 ± 0.041 | 0.325 ± 0.030 |
| 60 | 0.515 ± 0.016 | 0.343 ± 0.090 | 0.488 ± 0.012 | 0.495 ± 0.032 |
| 120 | 0.509 ± 0.079 | 0.601 ± 0.052 | 0.541 ± 0.065 | 0.570 ± 0.029 |
| C(ARKKAAKA)$_4$C (cyclized) | | | | |
| 1 | 0.058 ± 0.039 | 0.034 ± 0.019 | 0.022 ± 0.009 | 0.011 ± 0.005 |
| 6 | 0.245 ± 0.064 | 0.102 ± 0.012 | 0.126 ± 0.039 | 0.092 ± 0.014 |
| 12 | 0.474 ± 0.024 | 0.213 ± 0.048 | 0.251 ± 0.098 | 0.218 ± 0.047 |
| 60 | 0.554 ± 0.023 | 0.496 ± 0.016 | 0.506 ± 0.012 | 0.522 ± 0.009 |
| 120 | 0.525 ± 0.028 | 0.551 ± 0.031 | 0.538 ± 0.013 | 0.592 ± 0.019 |
| (ARKKAAKA)$_3$-ARKKCAKA | | | | |
| 1 | 0.081 ± 0.033 | 0.036 ± 0.008 | 0.033 ± 0.026 | 0.044 ± 0.019 |
| 6 | 0.363 ± 0.083 | 0.281 ± 0.011 | 0.253 ± 0.014 | 0.221 ± 0.031 |
| 12 | 0.544 ± 0.040 | 0.353 ± 0.007 | 0.317 ± 0.021 | 0.348 ± 0.042 |
| 60 | 0.621 ± 0.089 | 0.471 ± 0.043 | 0.513 ± 0.039 | 0.532 ± 0.011 |
| 120 | 0.647 ± 0.017 | 0.595 ± 0.028 | 0.522 ± 0.023 | 0.661 ± 0.017 |
| (ARKKAAKA)-(A)$_{16}$-(ARKKAAKA) | | | | |
| 1 | 0.020 ± 0.023 | 0.010 ± 0.008 | 0.027 ± 0.014 | 0.0 |
| 6 | 0.013 ± 0.007 | 0.018 ± 0.018 | 0.042 ± 0.041 | 0.0 |
| 12 | 0.010 ± 0.007 | 0.025 ± 0.011 | 0.042 ± 0.023 | 0.008 ± 0.012 |
| 60 | 0.017 ± 0.014 | 0.018 ± 0.020 | 0.061 ± 0.067 | 0.015 ± 0.012 |
| 120 | 0.069 ± 0.035 | 0.043 ± 0.020 | 0.092 ± 0.042 | 0.003 ± 0.002 |
| (ARKKAAKA)$_3$-(VL)$_4$ | | | | |
| 1 | 0.082 ± 0.027 | 0.055 ± 0.041 | 0.035 ± 0.009 | 0.058 ± 0.054 |
| 6 | 0.288 ± 0.045 | 0.292 ± 0.047 | 0.189 ± 0.066 | 0.202 ± 0.042 |
| 12 | 0.412 ± 0.035 | 0.441 ± 0.058 | 0.376 ± 0.001 | 0.371 ± 0.031 |
| 60 | 0.441 ± 0.010 | 0.588 ± 0.027 | 0.561 ± 0.035 | 0.532 ± 0.023 |
| 120 | 0.463 ± 0.029 | 0.575 ± 0.057 | 0.480 ± 0.035 | 0.485 ± 0.022 |
| (AKKARA)$_6$ | | | | |
| 1 | 0.137 ± 0.058 | 0.055 ± 0.033 | 0.029 ± 0.020 | 0.044 ± 0.011 |
| 6 | 0.393 ± 0.006 | 0.134 ± 0.009 | 0.113 ± 0.083 | 0.151 ± 0.015 |
| 12 | 0.434 ± 0.002 | 0.271 ± 0.018 | 0.195 ± 0.073 | 0.259 ± 0.057 |
| 60 | 0.572 ± 0.023 | 0.534 ± 0.033 | 0.524 ± 0.042 | 0.503 ± 0.039 |
| 120 | 0.588 ± 0.018 | 0.601 ± 0.038 | 0.603 ± 0.065 | 0.529 ± 0.009 |
| (ARKKAAKA)$_3$-(VL)$_3$ | | | | |
| 1 | 0.064 ± .046 | 0.070 ± .036 | 0.030 ± 0.020 | 0.005 + 0.007 |
| 6 | 0.298 ± .049 | 0.250 ± .012 | 0.234 ± 0.032 | 0.153 ± 0.031 |
| 12 | 0.457 ± .016 | 0.241 ± .076 | 0.247 ± 0.031 | 0.276 ± 0.033 |
| 60 | 0.479 ± .006 | 0.453 ± .029 | 0.474 ± 0.011 | 0.491 ± 0.029 |
| 120 | 0.516 ± .065 | 0.457 ± .010 | 0.496 ± 0.028 | 0.471 ± 0.013 |
| (VL)$_2$-(ARKKAAKA)$_3$-ARKKCAKA | | | | |
| 1 | 0.091 ± .053 | 0.080 ± .036 | 0.071 ± 0.056 | 0.077 ± 0.055 |
| 6 | 0.432 ± .086 | 0.218 ± .026 | 0.233 ± 0.025 | 0.217 ± 0.154 |
| 12 | 0.484 ± .012 | 0.365 ± .076 | 0.290 ± 0.047 | 0.380 ± 0.045 |
| 60 | 0.550 ± .027 | 0.483 ± .070 | 0.456 ± 0.029 | 0.461 ± 0.05 |
| 120 | 0.533 ± .017 | 0.674 ± .105 | 0.515 ± 0.005 | 0.483 ± 0.044 |

TABLE 2B

Effect of Peptides on anti-Factor Xa Activity of Unfractionated Heparin

| μg/ml Peptide | Unfractionated Heparin Neutralized, U/ml | | | |
|---|---|---|---|---|
| | Citrate | A Plasma | B Plasma | C Plasma |
| Protamine | | | | |
| 1 | 0.126 ± 0.042 | 0.241 ± 0.026 | 0.268 ± 0.028 | 0.161 ± 0.030 |
| 6 | 0.475 ± 0.017 | 0.442 ± 0.012 | 0.423 ± 0.035 | 0.425 ± 0.012 |
| 12 | 0.429 ± 0.010 | 0.466 ± 0.023 | 0.448 ± 0.041 | 0.405 ± 0.035 |
| 60 | 0.406 ± 0.023 | 0.380 ± 0.037 | 0.387 ± 0.047 | 0.350 ± 0.019 |
| 120 | 0.374 ± 0.030 | 0.372 ± 0.024 | 0.374 ± 0.034 | 0.310 ± 0.024 |
| (ARKKAAKA)$_4$ | | | | |
| 1 | 0.056 ± 0.019 | 0.069 ± 0.023 | 0.124 ± 0.047 | 0.076 ± 0.014 |
| 6 | 0.423 ± 0.014 | 0.334 ± 0.016 | 0.361 ± 0.038 | 0.397 ± 0.004 |
| 12 | 0.370 ± 0.020 | 0.412 ± 0.010 | 0.395 ± 0.012 | 0.396 ± 0.018 |
| 60 | 0.378 ± 0.023 | 0.389 ± 0.018 | 0.442 ± 0.056 | 0.401 ± 0.012 |
| 120 | 0.361 ± 0.028 | 0.364 ± 0.032 | 0.392 ± 0.075 | 0.374 ± 0.020 |
| C-(ARKKAAKA)$_4$-C | | | | |
| 1 | 0.131 ± 0.070 | 0.157 ± 0.032 | 0.194 ± 0.066 | 0.078 ± 0.027 |
| 6 | 0.590 ± 0.024 | 0.442 ± 0.031 | 0.426 ± 0.064 | 0.447 ± 0.054 |
| 12 | 0.560 ± 0.012 | 0.579 ± 0.128 | 0.552 ± 0.056 | 0.583 ± 0.066 |
| 60 | 0.560 ± 0.018 | 0.605 ± 0.088 | 0.566 ± 0.036 | 0.572 ± 0.076 |
| 120 | 0.530 ± 0.019 | 0.618 ± 0.051 | 0.512 ± 0.032 | 0.580 ± 0.051 |
| (ARKKAAKA)$_3$-ARKKCAKA | | | | |
| 1 | 0.070 ± 0.025 | 0.042 ± 0.029 | 0.104 ± 0.003 | 0.064 ± 0.012 |
| 6 | 0.416 ± 0.039 | 0.438 ± 0.004 | 0.453 ± 0.012 | 0.458 ± 0.049 |
| 12 | 0.392 ± 0.034 | 0.417 ± 0.024 | 0.445 ± 0.024 | 0.464 ± 0.091 |
| 60 | 0.373 ± 0.023 | 0.375 ± 0.043 | 0.328 ± 0.008 | 0.434 ± 0.053 |
| 120 | 0.362 ± 0.015 | 0.358 ± 0.015 | 0.323 ± 0.039 | 0.424 ± 0.027 |
| (ARKKAAKA)-(A)$_{16}$-(ARKKAAKA) | | | | |
| 1 | 0.040 ± 0.017 | 0.080 ± 0.050 | 0.0 | 0.0 |
| 6 | 0.064 ± 0.020 | 0.045 ± 0.029 | 0.005 ± 0.007 | 0.008 ± 0.012 |
| 12 | 0.047 ± 0.025 | 0.026 ± 0.018 | 0.008 ± 0.012 | 0.0 |
| 60 | 0.156 ± 0.046 | 0.100 ± 0.021 | 0.084 ± 0.034 | 0.022 ± 0.017 |
| 120 | 0.199 ± 0.039 | 0.112 ± 0.036 | 0.084 ± 0.018 | 0.090 ± 0.019 |
| (ARKKAAKA)$_3$-(VL)$_4$ | | | | |
| 1 | 0.072 ± 0.042 | 0.258 ± 0.153 | 0.247 ± 0.034 | 0.116 ± 0.032 |
| 6 | 0.651 ± 0.084 | 0.580 ± 0.067 | 0.597 ± 0.046 | 0.582 ± 0.035 |
| 12 | 0.505 ± 0.049 | 0.562 ± 0.050 | 0.586 ± 0.053 | 0.554 ± 0.049 |
| 60 | 0.528 ± 0.039 | 0.535 ± 0.054 | 0.444 ± 0.019 | 0.539 ± 0.010 |
| 120 | 0.510 ± 0.117 | 0.490 ± 0.049 | 0.279 ± 0.038 | 0.460 ± 0.057 |
| (AKKARA)$_6$ | | | | |
| 1 | 0.108 ± 0.056 | 0.206 ± 0.063 | 0.179 ± 0.005 | 0.125 ± 0.042 |
| 6 | 0.547 ± 0.019 | 0.530 ± 0.045 | 0.536 ± 0.023 | 0.533 ± 0.032 |
| 12 | 0.572 ± 0.040 | 0.556 ± 0.032 | 0.581 + 0.023 | 0.590 ± 0.020 |
| 60 | 0.555 ± 0.002 | 0.562 ± 0.009 | 0.552 ± 0.014 | 0.625 ± 0.043 |
| 120 | 0.589 ± 0.025 | 0.511 ± 0.039 | 0.519 ± 0.016 | 0.575 ± 0.013 |
| (ARKKAAKA)$_3$--(VL)$_3$ | | | | |
| 1 | 0.150 ± 0.023 | 0.249 ± 0.129 | 0.142 ± 0.040 | 0.114 + 0.056 |
| 6 | 0.576 ± 0.060 | 0.667 + 0.019 | 0.598 + 0.016 | 0.572 ± 0.018 |
| 12 | 0.595 ± 0.021 | 0.570 ± 0.119 | 0.585 ± 0.005 | 0.575 ± 0.013 |
| (VL)$_2$-(ARKKAAKA)$_3$-ARKKCAKA | | | | |
| 1 | 0.262 ± 0.101 | 0.240 ± 0.061 | 0.259 ± 0.063 | 0.233 ± 0.075 |
| 6 | 0.597 ± 0.034 | 0.574 ± 0.014 | 0.550 ± 0.061 | 0.559 ± 0.014 |
| 12 | 0.534 ± 0.056 | 0.618 ± 0.014 | 0.586 ± 0.001 | 0.526 ± 0.031 |

TABLE 2C

Effect of Peptides on Anti-Factor Xa Activity of the
Non-Heparin Glycosaminoglycan Organan ®

| µg/ml Peptide | Organan Neutralized, U/ml | | | |
|---|---|---|---|---|
| | Citrate | A Plasma | B Plasma | C Plasma |
| Protamine | | | | |
| 1 | 0.030 ± 0.015 | 0.027 ± 0.004 | 0.021 ± 0.007 | 0.017 ± 0.006 |
| 6 | 0.093 ± 0.046 | 0.050 ± 0.025 | 0.040 ± 0.018 | 0.034 ± 0.021 |
| 12 | 0.308 ± 0.017 | 0.016 ± 0.013 | 0.065 ± 0.014 | 0.043 ± 0.018 |
| 60 | 0.322 ± 0.038 | 0.140 ± 0.021 | 0.241 ± 0.032 | 0.234 ± 0.025 |
| 120 | 0.136 ± 0.034 | 0.340 ± 0.021 | 0.364 ± 0.013 | 0.318 ± 0.019 |
| (ARKKAAKA)$_4$ | | | | |
| 1 | 0.021 ± 0.022 | 0.026 ± 0.021 | 0.025 ± 0.009 | 0.020 ± 0.012 |
| 6 | 0.172 ± 0.028 | 0.061 ± 0.006 | 0.057 ± 0.022 | 0.074 ± 0.056 |
| 12 | 0.178 ± 0.021 | 0.082 ± 0.012 | 0.110 ± 0.021 | 0.116 ± 0.021 |
| 60 | 0.298 ± 0.044 | 0.211 ± 0.029 | 0.192 ± 0.009 | 0.182 ± 0.006 |
| 120 | 0.366 ± 0.019 | 0.286 ± 0.040 | 0.302 ± 0.012 | 0.299 ± 0.024 |
| C-(ARKKAAKA)$_4$-C | | | | |
| 1 | 0.072 ± 0.052 | 0.016 ± 0.012 | 0.038 ± 0.036 | 0.008 ± 0.005 |
| 6 | 0.099 ± 0.062 | 0.074 ± 0.049 | 0.027 ± 0.016 | 0.030 ± 0.009 |
| 12 | 0.180 ± 0.023 | 0.050 ± 0.031 | 0.082 ± 0.029 | 0.063 ± 0.025 |
| 60 | 0.319 ± 0.016 | 0.287 ± 0.033 | 0.282 ± 0.020 | 0.250 ± 0.030 |
| 120 | 0.340 ± 0.010 | 0.389 ± 0.118 | 0.374 ± 0.062 | 0.335 ± 0.012 |
| (ARKKAAKA)$_3$-ARKKCAKA | | | | |
| 1 | 0.028 ± 0.040 | 0.060 ± 0.034 | 0.011 ± 0.010 | 0.013 ± 0.006 |
| 6 | 0.118 ± 0.127 | 0.062 ± 0.028 | 0.040 ± 0.022 | 0.054 ± 0.015 |
| 12 | 0.134 ± 0.147 | 0.068 ± 0.016 | 0.061 ± 0.032 | 0.089 ± 0.034 |
| 60 | 0.234 ± 0.276 | 0.163 ± 0.017 | 0.172 ± 0.013 | 0.174 ± 0.019 |
| 120 | 0.366 ± 0.358 | 0.244 ± 0.024 | 0.286 ± 0.010 | 0.236 ± 0.019 |
| (ARKKAAKA)$_3$-(VL)$_4$ | | | | |
| 1 | 0.078 ± 0.031 | 0.028 ± 0.016 | 0.026 ± 0.011 | 0.035 ± 0.010 |
| 6 | 0.114 ± 0.007 | 0.050 ± 0.026 | 0.049 ± 0.021 | 0.075 ± 0.005 |
| 12 | 0.227 ± 0.017 | 0.109 ± 0.019 | 0.083 ± 0.016 | 0.114 ± 0.010 |
| 60 | 0.380 ± 0.021 | 0.281 ± 0.036 | 0.258 ± 0.013 | 0.248 ± 0.020 |
| 120 | 0.345 ± 0.032 | 0.366 ± 0.010 | 0.320 ± 0.010 | 0.296 ± 0.011 |

Neutralizing Lovenox® Activity in Blood from Patients Treated with Lovenox®

The peptides having the sequences of ARKKAAKAARKKAAKAARKKAAKAVLVLVLVL (SEQ ID NO:5), ARKKAAKAARKKAAKAARKKAAKAVLVLVL (SEQ ID NO:7), VLVLARKKAAKAPARKKAAKAVLVL (SEQ ID NO: 14), ARKKAAKA(A$_{16}$)ARKKAAKA (SEQ ID NO:30), (ARKKAAKA)$_4$ (SEQ ID NO:31), (AKKARA)$_6$ (SEQ ID NO:32), (ARKKAAKA)$_3$ARKKCAKA (SEQ ID NO:33), C(ARKKAAKA)$_4$C (SEQ ID NO:34), and VLVL(ARKKAAKA)ARKKCAKA (SEQ ID NO:38) were synthesized as described in Example 1.

Blood was obtained from volunteers who were being treated with Lovenox® for their medical conditions after obtaining signatures on informed consent forms as approved by the Institutional Review Board. The assays to test neutralization of Lovendx® were performed as described for Table 2. A dose response from 1-60 µg/ml was evaluated as in Table 2.

Results.

The results are summarized in Table 3. The dose response pattern for the effective peptides was similar to the dose response in control plasma to which Lovenox® had been added. For clarity, only the data for the 12 µg/ml dose of peptide are reported in Table 3. Each data point represents the mean and standard deviation of triplicate analyses on the same sample of blood from each patient.

Whereas all the concatameric peptides neutralized Lovenox® effectively in blood to which Lovenox® was added in vitro (see Table 2), neutralization patterns were very different in samples from the patients (Table 3). Without wishing to be bound by any particular theory, it is possible that Lovenox® is metabolized to smaller yet still anticoagulantly active chains as it passes through the circulation. Peptide (ARKKAAKA)$_3$VLVLVLVL (SEQ ID NO:5) was the most consistently effective in neutralizing clinically significant amounts of Lovenox®. However, in some patients other peptides were at least as effective as (ARKKAAKA)$_3$VLVLVLVL (SEQ ID NO:5). Further studies performed in vitro with control plasma, in which the effectiveness of the optimal dose of (ARKKAAKA)$_3$VLVLVLVL has been enhanced by addition of other concatameric peptides, suggest that Lovenox® contains fragments that interact preferentially with different peptide structures. The data from the patients suggest that this is also true of the fragments obtained during passage of Lovenox® through the circulation, and therefore that mixtures of peptides might be useful formulations for treatment of patients.

All tested peptides, with the exception of (ARKKAAKA)(A$_{16}$)(ARKKAAKA) (SEQ ID NO:30) and VLVLARKKAAKAPARKKAAKAVLVL (SEQ ID NO:14), were much more effective than Protamine, consistent with the known lack of clinically significant response of Lovenox®-treated patients to Protamine. Protamine neutralized Lovenox® in the blood of just one patient; probably because Lovenox was administered shortly before the blood was drawn, and thus had not been extensively metabolized.

initial setting). The abscissa (X-axis) represents time. Each tracing was taken for a period of 5 minutes.

The peptides (ARKKAAKA)$_4$ (SEQ ID NO:31), ARK-KAAKA(A$_{16}$)ARKKAAKA (SEQ ID NO:30), (ARK-KAAKA)$_3$ARKKCAKA (SEQ ID NO:33), (ARK-KAAKA)$_3$ VLVLVLVL (SEQ ID NO:5), C(ARKKAAKA)$_4$

TABLE 3

Effect of Peptides on Neutralizing Lovenox ® Activity in Blood from Patients Treated with Lovenox ®

| | Lovenox ® Neutralized, U/ml Patient Number | | | | | | | | |
|---|---|---|---|---|---|---|---|---|---|
| Peptide, 12 µg/ml | 1 | 2 | 3 | 4 | 5 | 8 | 9 | 10 | 11 |
| Protamine | 0.016 ± 0.016 | 0.022 ± 0.018 | 0 | 0.092 ± 0.068 | 0.013 ± 0.018 | 0.018 ± 0.017 | 0.244 ± 0.056 | 0.069 ± 0.023 | 0.021 ± 0.027 |
| (ARKKAAKA)$_4$ | 0.116 ± 0.008 | 0.073 ± 0.012 | 0.105 ± 0.071 | 0.225 ± 0.068 | 0.194 ± 0.069 | 0.289 ± 0.206 | 0.283 ± 0.058 | 0.194 ± 0.016 | 0.135 ± 0.038 |
| C(ARKKAAKA)$_4$C | 0.164 ± 0.019 | 0.132 ± 0.044 | 0.119 ± 0.033 | 0.337 ± 0.063 | 0.230 ± 0.051 | 0.163 ± 0.023 | 0.418 ± 0.036 | 0.302 ± 0.037 | 0.175 ± 0.084 |
| (ARKKAAKA)$_3$-ARKKCAKA | 0.096 ± 0.022 | 0.079 ± 0.014 | 0.084 ± 0.005 | 0.305 ± 0.038 | 0.274 ± 0.080 | 0.165 ± 0.047 | 0.232 ± 0.048 | 0.218 ± 0.018 | 0.157 ± 0.112 |
| (ARKKAAKA)(A$_{16}$)-(ARKKAAKA) | 0 | 0.011 ± 0.012 | 0.055 ± 0.043 | 0.035 ± 0.050 | 0.005 ± 0.008 | 0 | 0.009 ± 0.007 | 0.062 ± 0.010 | 0.007 + 0.005 |
| (ARKKAAKA)$_3$-VLVLVLVL | 0.213 ± 0.191 | 0.252 ± 0.038 | 0.302 ± 0.067 | 0.439 ± 0.037 | 0.265 ± 0.048 | 0.268 ± 0.007 | 0.478 ± 0.115 | 0.436 ± 0.093 | 0.398 ± 0.133 |
| (AKKARA)$_6$ | 0.026 ± 0.020 | 0.096 ± 0.063 | 0 | 0.171 ± 0.035 | 0.122 ± 0.021 | 0.128 ± 0.008 | 0.180 ± 0.058 | 0.173 ± 0.058 | 0.310 ± 0.231 |
| VLVLARKKAAKA-PARKKAAKAVLVL | 0.027 ± 0.019 | 0.012 ± 0.030 | 0.021 ± 0.030 | 0.022 ± 0.032 | 0 | 0.018 ± 0.016 | 0.007 ± 0.010 | 0.025 ± 0.035 | 0.050 ± 0.036 |
| (ARKKAAKA)$_3$ VLVLVL | 0.016 ± 0.012 | 0.030 ± 0.022 | 0.043 ± 0.031 | 0.122 ± 0.054 | 0.109 ± 0.073 | 0.104 ± 0.076 | 0.187 ± 0.099 | 0.133 ± 0.034 | 0.142 ± 0.040 |
| VLVL(ARKKAAKA)$_3$-ARKKCAKA | 0.043 ± 0.042 | 0.335 ± 0.075 | 0.008 ± 0.015 | 0.172 ± 0.106 | 0.110 ± 0.059 | 0.329 ± 0.228 | 0.200 ± 0.024 | 0.184 ± 0.072 | 0.240 ± 0.024 |

EXAMPLE 3

Platelet Aggregation Studies

Plasma from six volunteers was tested with various aggregation inducing agents, at several concentrations of each agent, and with six different peptides of the invention. The effect of heparin-binding peptides of the invention on platelet aggregation was determined using standard procedures as previously described. The six peptides which were synthesized and tested were: (ARKKAAKA)$_4$ (SEQ ID NO:31), ARKKAAKA(A$_{16}$)ARKKAAKA (SEQ ID NO:30), (ARK-KAAKA)$_3$ARKKCAKA (SEQ ID NO:33), (ARK-KAAKA)$_3$ VLVLVLVL (SEQ ID NO:5), C(ARKKAAKA)$_4$ C (SEQ ID NO:34), and (AKKARA)$_6$ (SEQ ID NO:32).

The aggregation-inducing agents tested were: collagen, adenosine diphosphate (ADP), ristocetin, epinephrine, the thrombin receptor peptide SFFLRN, and calcium ionophore A23187. Platelets were subjected to protamine, or to SEQ ID NOS:31, 33, 30, 5, 34, or 32 at 12 µg/ml, and Lovenox® at 0.5 U/ml. Platelet aggregation in response to agonists was monitored and percent aggregation was determined over a five minute interval.

The agonist was added after equilibration of the platelets for one minute.

Results. Representative graphic profiles for the effects of two of the tested peptides in the presence of the aggregation-inducing agent collagen (1.25 µg/ml) are provided in FIGS. 2A to 2E. The data are representative of multiple experiments. "Control" is platelet-rich plasma alone with each agonist. "Lovenox," indicates that the agonist was added in the presence of 0.5 U/ml of Lovenox®. The ordinate (Y-axis) represents the inverse of % aggregation (90% is the C (SEQ ID NO:34), and (AKKARA)$_6$ (SEQ ID NO:32) caused no significant inhibition or enhancement of aggregation in the presence of any of the aggregation-inducing agents listed above. The results demonstrate that the heparin-binding peptides of the invention do not have any deleterious effects on platelet aggregation in the presence of any of the agonists used.

EXAMPLE 4

Effects of Heparin-Binding Peptides on Thrombin Neutralization in the Presence of Unfractionated Heparin It was determined whether heparin-binding peptides of the invention can neutralize unfractionated heparin using the thrombin neutralization assay. The six peptides that were synthesized and used in this Example are: (ARKKAAKA)$_3$ VLVLVLVL (SEQ ID NO:5); (ARKKAAKA)(A$_{16}$)(ARK-KAAKA) (SEQ ID NO:30); (ARKKAAKA)$_4$ (SEQ ID NO:31); (AKKARA)$_6$ (SEQ ID NO:32); (ARKKAAKA)$_3$ (ARKKCAKA) (SEQ ID NO:33); and cyclized C(ARK-KAAKA)$_4$C (SEQ ID NO:34); Citrated plasma was pipetted into a glass tube. Thrombin was added, the tube was manually rotated, and clotting time was determined by observation of clot formation. Normal clotting time is 19-22 seconds.

As a control, to assess the effect of heparin on clot formation, unfractionated heparin was added to the plasma at 0.5 IU anti-thrombin activity/ml and then thrombin was added. Clotting time in the presence of heparin alone was greater than 3 minutes.

To test the effect of peptides, heparin and six peptides at the concentrations indicated in Table 4 were added to the plasma, the mixture was allowed to stand at room temperature for 1 minute, and thrombin was added. The time for the clot to form is indicated. Experiments were performed using plasma from three volunteers—A, B, and C.

Results. The five high-affinity peptides of the invention completely inhibited the effect of unfractionated heparin on thrombin-induced clot formation at 4.0-5.0 µg/ml, lower concentrations than required for inhibition of anti-Factor Xa activity. Furthermore, the peptides of the invention were as effective as protamine. These results are summarized in Table 4. The column headings A, B, and C refer to plasma derived from the three different volunteers. Higher peptide concentrations (up to 10 µg/ml) gave essentially the same result as 5.0 µg/ml. Peptides (ARKKAAKA)$_4$ (SEQ ID NO:31), (ARKKAAKA)$_3$ARKKCAKA (SEQ ID NO:33), (ARKKAAKA)$_3$VLVLVLVL (SEQ ID NO:5) and (AKKARA)$_6$ (SEQ ID NO:32) were able to totally neutralize heparin at 4.0-5.0 µg/ml. C(ARKKAAKA)$_4$C (SEQ ID NO:34) was also effective. The peptide (ARKKAAKA)(A)$_{16}$(ARKKAA) (SEQ ID NO:30), which is outside the present invention, was ineffective.

It was also found that thrombin-induced clot formation (1 U/ml) in the presence of 1 U/ml unfractionated heparin was inhibited by 3.5-5 µg/ml peptide.

Thus, the high affinity heparin-binding peptides of the invention are believed to be useful alternatives for protamine for thrombin inhibition in patients treated with unfractionated heparin.

TABLE 4

Effects of peptides on thrombin neutralization in the presence of unfractionated heparin

| Peptide | Time for clot formation (sec.) | | |
|---|---|---|---|
| µg peptide/0.1 ml | A | B | C |
| (ARKKAAKA)$_4$ | | | |
| 0.50 | 19.67 + 1.25 | 24.00 + 0.82 | 20.67 + 0.94 |
| 0.40 | 18.67 ± 0.94 | 26.30 ± 1.25 | 22.67 ± 1.25 |
| 0.35 | 22.33 ± 0.47 | 39.00 ± 5.35 | 32.67 ± 0.47 |
| 0.30 | 56.33 ± 4.92 | 53.33 ± 1.25 | |
| C-(ARKKAAKA)$_4$-C | | | |
| 0.50 | 23.67 ± 2.05 | 34.33 + 1.25 | 43.00 ± 2.45 |
| 0.40 | 29.00 ± 0.82 | 47.67 ± 8.34 | 56.33 ± 1.70 |
| 0.35 | 37.67 ± 5.25 | | |
| 0.30 | | | |
| (ARKKAAKA)$_3$-ARKKCAKA | | | |
| 0.50 | 22.00 + 1.41 | 18.00 + 0.00 | 17.33 + 0.47 |
| 0.40 | 27.00 ± 1.41 | 19.00 ± 1.63 | 26.67 ± 1.25 |
| 0.35 | 29.33 ± 1.89 | 25.00 ± 2.45 | |
| 0.30 | 45.00 ± 1.63 | 24.00 ± 1.41 | 35.33 ± 2.05 |
| (ARKKAAKA)-(A)$_{16}$-(ARKKAAKA) | | | |
| 7.5 | 58.67 ± 1.89 | | 180.0 ± 0.00 |
| 7.0 | 61.00 ± 2.94 | 85.67 ± 3.30 | 47.67 ± 3.77 |
| 6.5 | 76.33 ± 4.19 | | 48.67 ± 7.72 |
| 6.0 | | 55.00 ± 4.08 | |
| (ARKKAAKA)$_3$-(VL)$_4$ | | | |
| 0.50 | 17.67 + 1.25 | 23.67 ± 0.47 | 25.67 ± 0.47 |
| 0.40 | 20.00 ± 0.82 | 26.67 ± 1.25 | 32.33 ± 2.05 |
| 0.35 | | 28.33 ± 1.70 | 45.33 ± 2.05 |
| 0.30 | 37.00 ± 2.16 | 40.00 ± 1.63 | |

TABLE 4-continued

Effects of peptides on thrombin neutralization in the presence of unfractionated heparin

| Peptide | Time for clot formation (sec.) | | |
|---|---|---|---|
| µg peptide/0.1 ml | A | B | C |
| (AKKARA)$_6$ | | | |
| 0.50 | 20.67 + 0.94 | 24.00 + 0.82 | 19.33 + 0.47 |
| 0.40 | 21.00 ± 1.41 | 25.33 ± 1.25 | 21.00 ± 2.16 |
| 0.35 | 20.00 ± 0.00 | 25.33 ± 0.47 | 23.00 ± 0.82 |
| 0.30 | 29.33 ± 1.25 | 39.00 ± 3.27 | 28.67 ± 4.64 |
| 0.25 | 52.33 ± 6.13 | | 52.67 ± 3.68 |

EXAMPLE 5

Hemodynamic Effects of Heparin-Binding Peptides In Vivo

Rats were sedated, and catheters were inserted into the femoral vein and femoral artery. The femoral artery catheter was hooked up to the computerized monitoring system, and injections were made through the femoral vein. Peptides were injected into rats without prior injection of Lovenox. Two or more rats (300-350 grams) were treated with 2 mg protamine or peptide. Representative blood pressure tracings are shown in FIG. 3.

At the times indicated in the figures, the following actions were taken: administration of saline to insure that the animal and intubations were stable; administration of test peptide or protamine alone; then administration of protamine. The final administration of protamine was performed to see whether a lack of change in blood pressure was due to an innate resistance of the animal to the hypotensive effects of protamine, and interestingly showed that some of the peptides may have in fact rendered the animals resistant to protamine.

Protamine caused a rapid reduction of about 25-35 mm Hg in both systolic and diastolic pressures beginning within less than a minute, reaching a nadir at about 4.5 minutes, and recovery after about 10-12 minutes.

(ARKKAAKA)$_4$ (SEQ ID NO:31) and (AKKARA)$_6$ (SEQ ID NO:6) caused a transient drop of about 30 mm Hg, which reached a nadir in 2 minutes and was reversed by 4 minutes. Peptide ARKKAAKA(A$_{16}$)ARKKAAKA (SEQ ID NO:30) did not affect blood pressure. In most rats no drop in blood pressure was seen with (ARKKAAKA)$_3$VLVLVLVL (FIG. 3-4), but in one rat a transient (1-2 minutes) drop was observed. The cyclized peptide C(ARKKAAKA)$_4$C (SEQ ID NO:34) and (ARKKAAKA)$_3$ARKKCAKA (SEQ ID NO:33) did not cause a change in blood pressure, and may have protected the animal against the blood pressure drop upon subsequent infusion of protamine. Heart rate in some cases showed an increase of about 10 bpm (normal approx. 320 bpm) at the time that the blood pressure was decreasing. Oxygen saturation and respiration were unaffected.

Next, experiments were performed in which the animals were treated with the peptides after the administration of the LMWH Lovenox®, as would happen in the clinical situation, because binding of peptides to LMWH would be expected to reduce the effects of the peptides on hemodynamic function. In the presence of LMWH, 10 out of 15 rats tested with protamine suffered a severe blood pressure drop ($\geq$30 mm Hg, lasting for 10 minutes) similar to animals given protamine in the absence of Lovenox® (FIG. 3-1). In contrast to this deleterious effect of protamine, in the presence of the LMWH Lovenox® the peptides showed little or no toxicity in terms of their effect on blood pressure, heart rate, respiration rate and oxygen saturation. The heart rate was normal in the peptide-treated animals, but the heart rate in the protamine-treated animals dropped to a nadir of about 80% of normal and then returned to normal in parallel with the change in blood pressure.

Next, the effects of protamine were compared to those of (ARKKAAKA)$_4$ (SEQ ID NO:31) and (ARKKAAKA)$_3$ ARKKCAKA (SEQ ID NO:33). The two peptides had no significant effect on blood pressure and heart rate. (ARKKAAKA)$_4$ (SEQ ID NO:31) prevented the protamine response and (ARKKAAKA)$_3$ARKKCAKA (SEQ ID NO:33) either totally prevented or allowed only a minimal response to protamine.

Next, two other peptides of the invention were tested. Cyclized C(ARKKAAKA)$_4$C (SEQ ID NO:34) and (ARKKAAKA)$_3$VLVLVLVL (SEQ ID NO:5) had no, or minimal, adverse effects on blood pressure or heart rate and the cyclized peptide was not toxic. Additional experiments showed that the peptides of the invention had no detectable negative effects.

The results of this Example of physiologic effects of peptides in the presence of the enoxaparin Lovenox® are summarized as follows:

(ARKKAAKA)$_4$ (SEQ ID NO: 31): All four rats tested showed no response with this peptide. Subsequent protamine caused major and prolonged drop in blood pressure and heart rate in two rats.

C(ARKKAAKA)$_4$C-cyclized (SEQ ID NO:34): All rats tested showed no response. Three of the four rats showed major responses to subsequent protamine.

(ARKKAAKA)$_3$ARKKCAKA (SEQ ID NO:33): All rats tested showed no response to peptide. One showed severe protamine response, and 4 showed mild response with rapid recovery.

(ARKKAAKA)$_3$VLVLVLVL (SEQ ID NO:5): Two out of five rats tested demonstrated drops of 30 and 45 mm Hg about 3 minutes after peptide injection and quick recovery within 1 minute. Response to subsequent protamine was deep.

In summary, representative peptides of the invention such as (ARKKAAKA)$_4$ (SEQ ID NO:31), (ARKKAAKA)$_3$ VLVLVLVL (SEQ ID NO:5), (ARKKAAKA)$_3$ ARKKCAKA (SEQ ID NO:33), and C(ARKKAAKA)$_4$C (SEQ ID NO:34), have no effect, or only minimal effect on blood pressure or heart rate when infused into rats in the presence of the LMWH Lovenox®, and some also are believed to render the animals resistant to a drop in blood pressure from a subsequent challenge with protamine. Thus, any of these peptides are believed to have a physiologic advantage over protamine in this important clinical consideration of maintenance of blood pressure. In addition, some of the tandem repeat peptides, singly or in combination, are suitable candidates for neutralization of UFH and LMWH in subjects who would benefit from such treatment.

EXAMPLE 6

In Vivo Neutralization of the LMWH Lovenox® in Rats

Experiments were performed to test the ability of heparin-binding peptides of the invention to neutralize low molecular weight heparins which are used clinically, such as Lovenox®. To this end, rats were cannulated in the jugular and femoral veins. Lovenox® was injected through the jugular vein, and three minutes later the peptide was injected via the jugular vein. The peptides tested included (ARKKAAKA)$_4$ (SEQ ID NO:31), C(ARKKAAKA)$_4$C (SEQ ID NO:34), (ARKKAAKA)$_3$ARKKCAKA (SEQ ID NO:33), and (ARKKAAKA)$_3$VLVLVLVL (SEQ ID NO:5). Blood was collected from the femoral vein. 0.1 ml was collected at each time point. Plasma was prepared from each tube, and the anti-Factor Xa assay was performed.

Figures 3, 4:
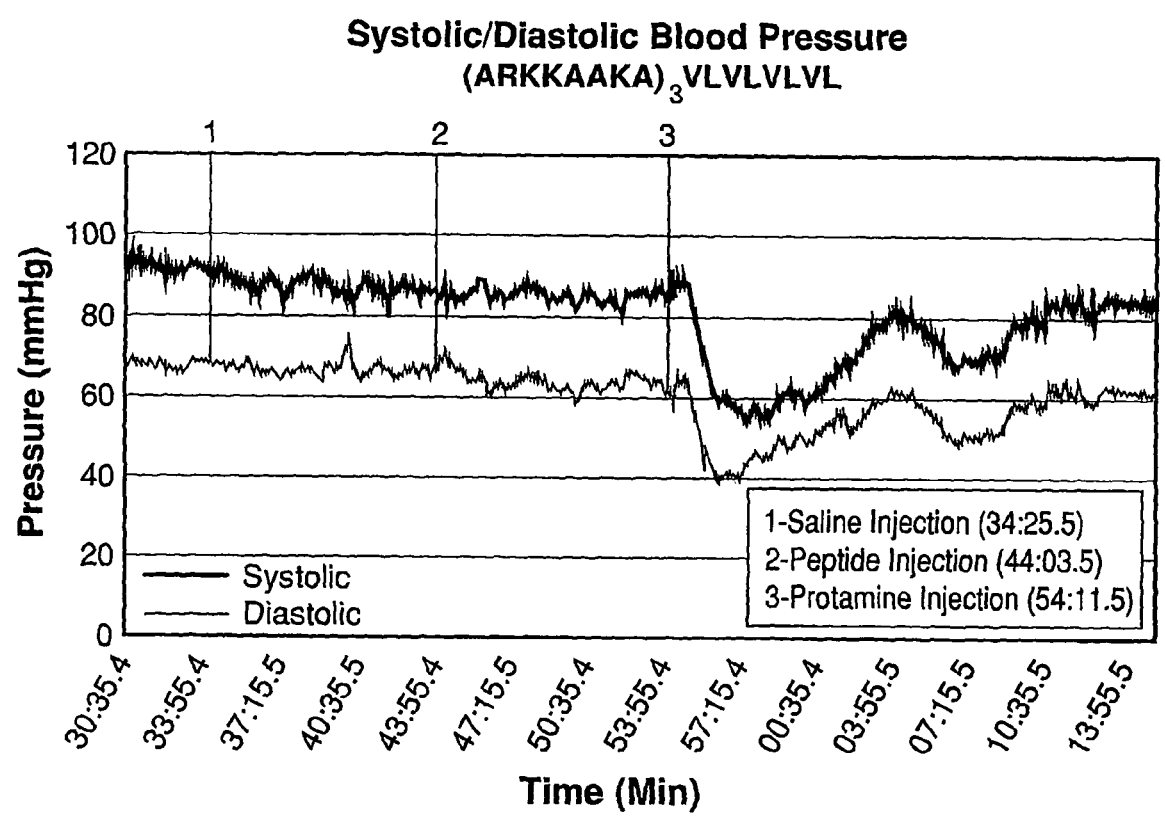
Figures 3, 4, 5:
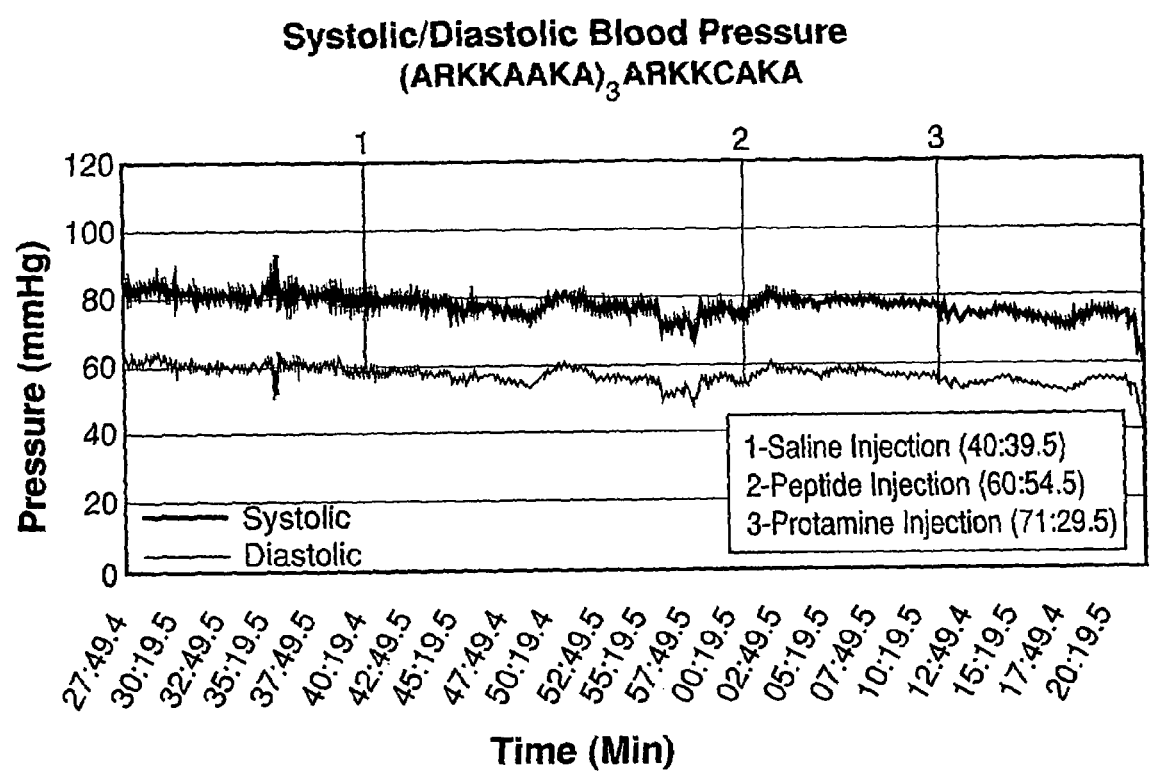
Figures 3, 4, 5, 6:
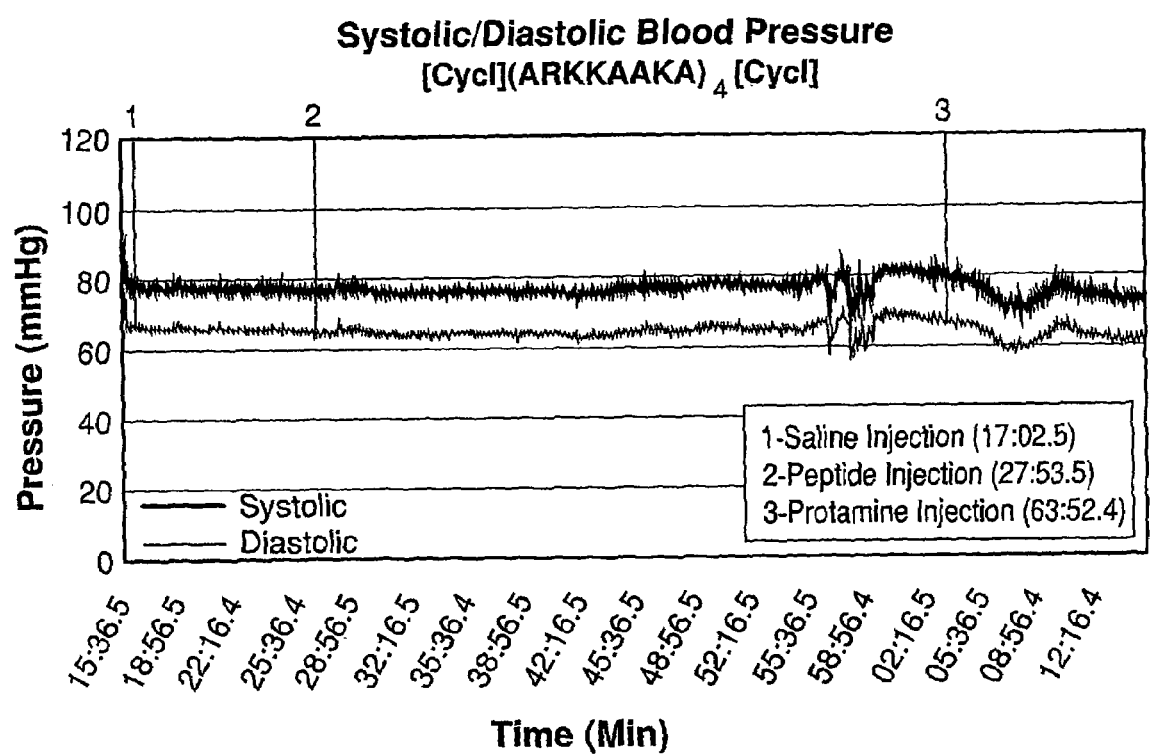
Figures 3, 4, 5, 6, 7:
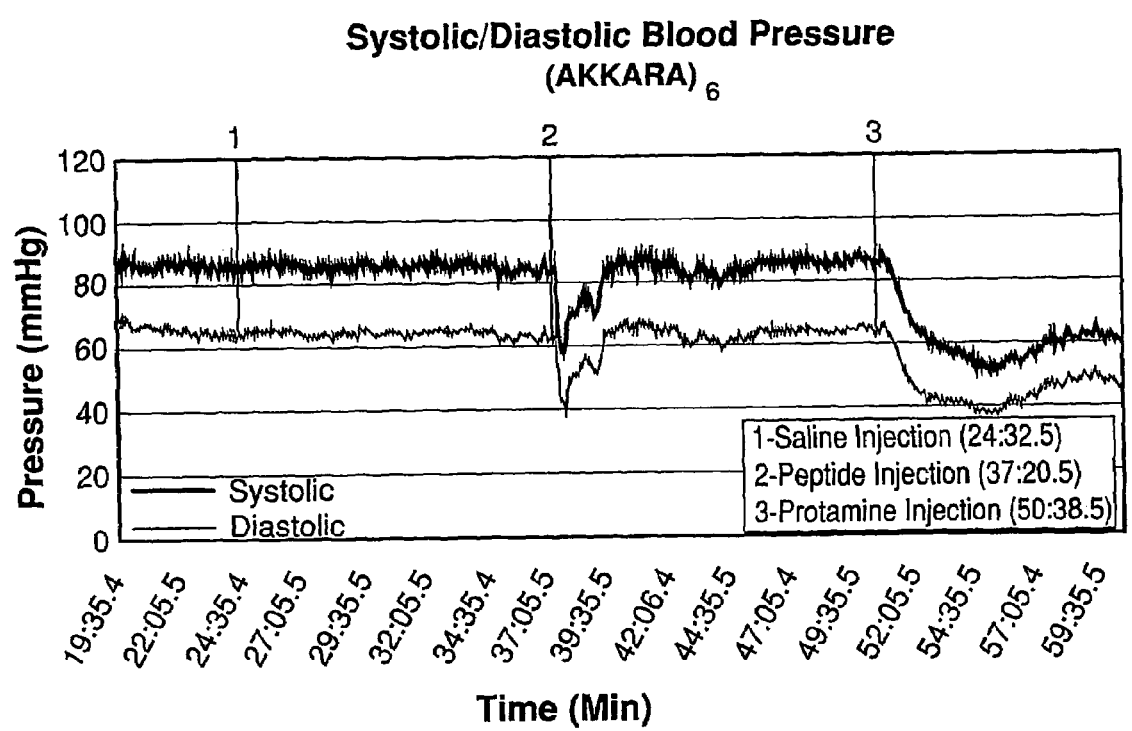
Figure 4A:
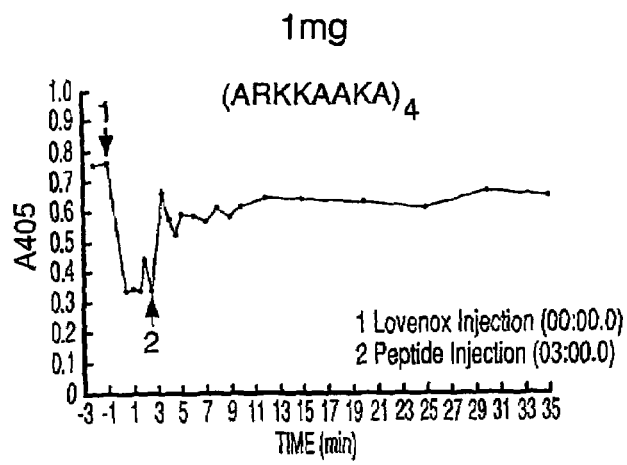
FIGS. 4A to 4D show the ability of representative peptides of the invention to neutralize the low molecular weight heparin enoxaparin sodium (Lovenox®, Aventis Pharmaceuticals, Inc.) in rats, as determined in an anti-Factor Xa assay. The events marked by arrows are indicated in the insert as "1 Lovenox injection (00:00.0)" and "2 Peptide Injection (03:00.0)". The graphs illustrate the response to 1.0 mg peptide/300 gm body weight of (ARKKAAKA)$_4$ (SEQ ID NO:31) (FIG. 4A), cyclized C(ARKKAAKA)$_4$C (SEQ ID NO:34) (FIG. 4B), (ARKKAAKA)$_3$ARKKCAKA (SEQ ID NO:33) (FIG. 4C), and (ARKKAAKA)$_3$VLVLVLVL (SEQ ID NO:5) (FIG. 4D). The ordinate represents absorbance at 405 nm and the abscissa represents time in minutes.
Figure 4B:
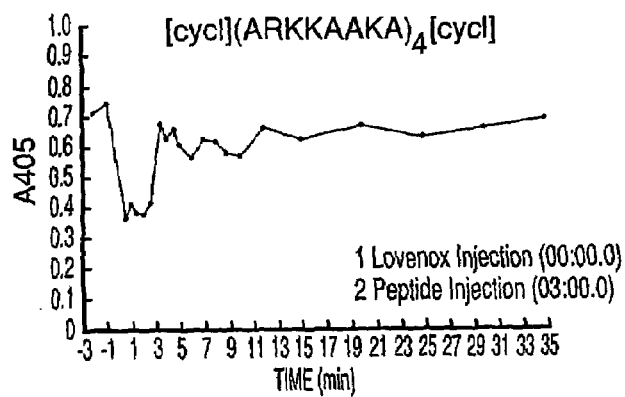
Figure 4C:
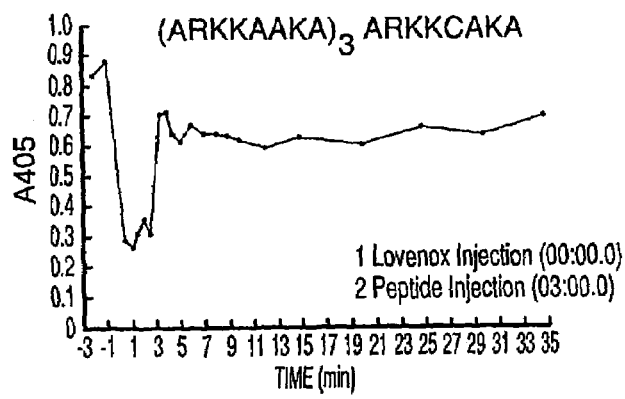
Figure 4D:
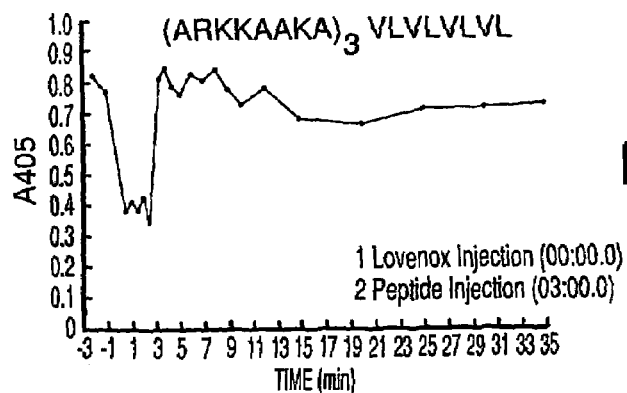

Results. The dose response of each peptide from 2 mg/300 gm to 0.5 mg/300 gm was tested and a representative dose (1.0 mg) is shown in FIG. 4. The -VLVLVLVL-containing peptide, (ARKKAAKA)$_3$VLVLVLVL (SEQ ID NO:5), was the most effective at the lowest dose and neutralized 0.5 to 0.7 U/ml of anti-Factor Xa activity of Lovenox®. The absorbance is inversely proportional to the heparin concentration. There is no heparin present when $A_{405}$=0.7, and about 1 U/ml when $A_{405}$=0.4. The events at the arrows are indicated in the box insert.

EXAMPLE 7

Binding of Heparin-Binding Peptides to Vascular Walls

Heparin-binding peptides of the invention, as described in Examples 1-6, are tested for their ability to bind to GAGs in vascular walls.

Materials

Fluorescein isothiocyanate (FITC), fluorescein-5 maleimide, and N-succinimidyl-S-acetylthioacetate (SATA), are from Pierce. The heparin-binding peptides are synthesized as described above. Random sequence peptides are prepared for use as negative controls.

Labeling with Fluorescein Derivatives

Heparin-binding peptides at concentrations of 5 mg/ml in a buffer containing 30 mmol/l sodium bicarbonate and 140 mmol/l NaCl, pH 9.2, are incubated for 1 hour in the dark with FITC at a final concentration of 250 μM as previously described (Sakharov et al., FEBS Letters, 2003, 537:6-10). Cysteine-containing peptides are prepared in 0.5 mM in Tris-buffered saline (TBS) containing 1 mM EDTA, and are incubated with fluorescein-5-maleimide at 1 mM for 1 hour. Unreacted groups are blocked with 5 mM N-ethylmaleimide. Unbound dye is separated from labeled molecules using gel filtration on Sephadex G-25 for larger peptides, or either CM-Sepharose ion-exchange chromatography with elution by a gradient of NaCl, or reverse-phase high-performance liquid chromatography for smaller peptides.

Delivery of Labeled Heparin-Binding Peptides into Carotid Artery Segments

A segment (approximately 1.2 cm) of the common carotid artery is removed from an anaesthetized rat and incubated for no longer than 1 hour in phenol red-free RPMI cell culture medium at 4° C. The labeled peptides are delivered into an arterial segment as previously described (Sakharov et al., FEBS Letters, 2003, 537:6-10). One end of the arterial segment is secured on a plastic tube connected to a needle attached to a syringe equipped with a manometer. To remove any remaining blood and to destroy the endothelium, the segment is rinsed with a few milliliters of RPMI and flushed with air for 5 minutes. Then, the segment is filled with RPMI containing a labeled heparin-binding peptide or control peptide at 1 mg/ml, the open end of the segment is closed with an atraumatic vascular clamp, and a pressure of 0.35 atm is applied for 20 minutes. Then, the clamp is removed, the segment is briefly washed with RPMI, and the distal half of the segment is removed and snap-frozen. The proximal part of the arterial segment, still connected to the needle, is perfused with RPMI through a peristaltic pump. The proximal half of the segment is cut off and snap-frozen.

Visualization and Quantification of Bound Heparin-Binding Peptides

Twenty μm cross-sections of frozen arterial segments are prepared, dried and viewed under a fluorescence microscope. To quantify the local concentration of fluorescence-labelled heparin-binding peptides within the vascular wall, the sections are eluted with TBS comprising 2.0 M NaCl. The amount of fluorescence in the eluate is measured with a LS50B spectrofluorometer (Perkin-Elmer) and the amount of eluted fluorescence-labelled compound is determined using a calibration curve obtained with dilutions of the compound. The local concentration of bound fluorescence-labelled compound is calculated as the ratio of the amount of eluted compound and the volume of the section of the vessel, which is typically saturated with fluorescence throughout the whole depth of the vessel wall. The volume is calculated as a product of the thickness of the section (20 μm), the perimeter of the vessel and the width of the vessel wall. For each heparin-binding peptide, the experiments are performed in duplicate. At least six sections are prepared from each specimen corresponding to a particular perfusion time and used for quantification of binding.

EXAMPLE 8

Heparin-Binding Peptides Inhibit Mast Cell Serine Proteases

According to the following methods, heparin-binding peptide inhibition of mast cell serine proteases is determined, including the rate of inhibition, and whether the inhibition is reversible.

Materials

Recombinant human βI-tryptase (rh-βI-tryptase) is purchased from Promega. The carbazole test is performed to ensure that heparin is not present in samples (Lundequist et al., Biochem. Pharmacol., 2003, 65:1171-1180). This assay detects heparin levels as low as ~1 μg. Rat chymase (rat mast cell protease 1, e.g., rMCP-1), is purified from peritoneal mast cells as described previously (Lundequist et al., Biochem. Pharmacol., 2003, 65:1171-1180). The chromogenic substrates S-2288 (H-D-Ile-Pro-Arg-pNA), S-2238 (H-D-Phe-Pip-Arg-pNA) and S-2586 (MeO-Suc-Arg-Pro-Tyr-pNA) are purchased from Chromogenix (Mölndal, Sweden). Heparin-binding peptides of the invention are prepared as described above (Examples 1-3).

Salmon Protamine ($M_r$~4500) is from Sigma. Polybrene (hexadimethrine bromide; 1,5-dimethyl-1,5-diaziundecamethylene polymethobromide) is obtained from Janssen Chimica. Porcine mucosal heparin ($M_r$~15,000) and Bovine α-thrombin are from various sources. Bovine pancreatic trypsin inhibitor (BPTI) is from Roche.

Cells

Peritoneal cells (~2-3% mast cells, the rest being ~50% macrophages and ~50% lymphocytes) from female C57BL/6 mice (~6 months of age) are collected by peritoneal lavage with 15 ml of cold phosphate-buffered saline (PBS), pH 7.4. Cells are centrifuged (300×g; 4° C.; 10 minutes), resuspended and cultured in serum-free medium H4281 (Sigma-Aldrich). The serum-free medium is supplemented with penicillin (100 IU/ml; GibcoBRL), streptomycin (100 mg/ml; Life Technologies, Inc.) and L-glutamine (10 mM). Cells are distributed in 24-well plates (~0.5×10$^6$ cells in 0.5 ml/well) and incubated at 37° C. in a humidified atmosphere of 5% $CO_2$.

Protease Enzymatic Assays

All enzymatic assays are performed at room temperature in 96-well microtiter plates. In standard incubations, 10 ng of rh-βI-tryptase is added to the wells in a total volume of 100 μl of PBS (pH 7.4; 0.1% Triton X-100). Heparin-binding peptides of the invention (inhibitors) in 10 μl of PBS (pH 7.4; 0.1% Triton X-100), are added and incubated for 10 minutes. Thereafter, 201 μl of a 2 mM solution (in $H_2O$) of S-2288 is added, and increased absorbance at 405 nm is monitored with a spectrophotometer. $IC_{50}$ values are determined by incubating increasing concentrations of inhibitor with protease for 10 minutes. Residual enzymatic activities of the serine proteases are monitored as for standard assays. The ratio of inhibited over uninhibited rates is plotted against the inhibitor concentration, and $IC_{50}$ values are determined by nonlinear regression analysis.

rMCP-1 (12.5 ng/sample in PBS, pH 7.4, 0.2% Triton X-100) is assayed with the chromogenic substrate S-2586. $IC_{50}$ values are determined as described above for rh-βI-tryptase. The values are corrected for the non-heparin-dependent activity and therefore the $IC_{50}$ values express the concentration needed for a 50% reduction of the heparin-stimulated activity.

Substrate concentrations ranging from 0.03 to 3.6 mM (S-2288) and 0.06 to 3.6 mM (S-2586) are used to determine binding activity. Absorbance changes are followed over 30 minutes with readings every 30 seconds. Initial reaction velocities, obtained within 5 minutes in all of the analyses, are used to calculate enzymatic activity. The data obtained are used for calculations of kinetic parameters after nonlinear regression analysis.

Thrombin Inactivation Assay For Chymase Activity

Heparin-binding peptides (inhibitors) at different concentrations are added to over-night cultures of peritoneal cells (see above), and incubated for 30 minutes before 1 μg of thrombin is added to the cells. Media samples (50 μl) are collected at different time points and stored at −20° C. Residual thrombin activities in the samples are assayed using S-2238: 10 μl of sample is mixed with 190 μl of PBS (pH 7.4) followed by the addition of 20 μl S-2238 solution (4 mM in $H_2O$) and recording of absorbance as described (Lundequist et al., Biochem. Pharmacol., 2003, 65:1171-1180).

Rate of Inhibition of Enzyme Activity

Either rh-βI-tryptase or rMCP-1 are incubated with various peptides of the invention as described above. After various times, the chromogenic substrates S-2288 (for rh-βI-tryptase) or S-2586 (for rMCP-1) are added and residual enzyme activities are measured as above.

Reversibility of Tryptase Inhibition by Heparin-Binding Peptides Using Exogenous Heparin The rh-βI-tryptase (10 ng in 100 μl PBS, pH 7.4, 0.1% Triton X-100) is incubated with heparin-binding peptides for various times. Next, heparin (50 μg; 5 μl of a 10 μg/μl solution in $H_2O$) is added. After 5 minutes in heparin, samples are treated with BPTI (1 μg; 5 μl of a 0.2 mg/μl solution in PBS) or buffer without BPTI. After an additional 5 minutes, residual activity is measured with the chromogenic substrate S-2288.

Heparin-Binding Peptide Inhibition of Tryptase-Induced Allergic Reaction

Tryptase induces cutaneous allergic reactions in sheep and when inhaled induces bronchoconstriction (Molinari et al., Am. J. Respir. Crit. Care Med., 1996, 154:649-653; Molinari et al., J. Appl. Physiol., 1995, 79:1966-1970). To test the ability of heparin-binding peptides of the invention to modulate the effects of tryptase on bronchoconstriction, some animals are treated first with a heparin-binding peptide of the invention, followed by inhalation treatment with tryptase. Some animals are treated with a heparin-binding peptide and tryptase simultaneously. Others receive the heparin-binding peptide following exposure to tryptase. Varied dosages of the heparin-binding peptides are tested. Bronchoconstriction is measured using standard techniques. Heparin-binding peptides of the invention are also tested for their ability to inhibit tryptase-induced cutaneous reactions in sheep.

EXAMPLE 9

Antimicrobial Activities of Heparin-Binding Peptides of the Invention

Materials and Methods

Microorganisms

*Enterococcus faecalis* 2374 (*E. faecalis*), *Escherichia coli* 37.4 (*E. coli*), *Pseudomonas aeruginosa* 15159 (*P. aeruginosa*), and *Proteus mirabilis* 4070 (*P. mirabilis*) are readily available and can be obtained from patients with chronic venous ulcers. The fungus *Candida albicans* 4435 (*C. albicans*) and other fingi are readily available and can be obtained from patients with various fungal conditions.

Viable Count Analysis

*E. faecalis*, *P. aeruginosa*, *E. coli*, and *P. mirabilis* are grown to mid-logarithmic phase in Todd-Hewitt medium as previously described (Andersson et al. Eur. J. Biochem. 2004, 271:1219-1226). Bacteria are washed and diluted in 10 mM, Tris pH 7.4 containing 5 mM glucose. Bacteria (50 µl; $2 \times 10^6$ bacteria/ml) are incubated at 37° C. overnight and the number of colony-forming units (c.f.u.) is determined.

Radial Diffusion Assay

Radial diffusion assays (RDA) are performed as described (Andersson et al. Eur. J. Biochem. 2004, 271:1219-1226). Briefly, bacteria (*E. coli*) or fungi (*C. albicans*) are grown to mid-logarithmic phase in 10 ml full-strength (3% w/v) trypticase soy broth (TSB) (Becton Dickinson). The microorganisms are washed once with 10 mM Tris, pH 7.4. Then $4 \times 10^6$ bacterial c.f.u. or $1 \times 10^5$ fungal c.f.u. are added to 5 ml of the underlay agarose gel, consisting of 0.03% (w/v) TSB, 1% (w/v) low-electroendosmosistype (Low-EEO) agarose (Sigma) and a final concentration of 0.02% (v/v) Tween 20 (Sigma). The underlay is poured into an 85-mm Petri dish. After agarose solidification, 4 mm-diameter wells are punched and 6 µl of test sample are added per well. Plates are incubated at 37° C. for 3 hours to allow diffusion of the peptides. The underlay gel is then covered with 5 ml of molten overlay (6% TSB, 1% Low-EEO agarose in dH$_2$O). Antimicrobial activity of a peptide is visualized as a clear zone around each well after 18-24 h of incubation at 37° C. for bacteria and 28° C. for *C. albicans*. For *E. coli* the dose-response characteristics of the RDA are used and the linear relationship between zone diameter and $\log_{10}$ concentration for LL-37 are determined by least mean squares regression analysis (Andersson et al. Eur. J. Biochem. 2004, 271:1219-1226). Heparin-binding peptides of the invention are tested in concentrations of 100 µM to determine the antibacterial effect, relative to the known peptide LL-37. To minimize variation between experiments, a LL-37 standard (100 µM) can be included on each plate. The antibacterial activity of the peptides can be presented in LL-37 equivalencies, where the zone inhibition obtained using 100 µM is indexed as 1. LL-37 yields clear inhibition zones at concentrations of 10 µM to 1000 µM and at higher concentrations LL-37 precipitates. Thus, the index expresses the level of antibacterial activity in relative terms. The activities of the heparin-binding peptides are also presented in radial diffusion units (RDU) [(diameter of clear zone in millimeters–well diameter)×(10)].

Heparin-Binding Assay

The heparin-binding peptides are tested for heparin-binding ability as described above or as described here. Peptides (1, 2 and 5 µg) are applied to nitrocellulose membranes (Hybond™-C, Amersham Biosciences). Membranes are blocked (NaCl/P$_i$ pH 7.4, 3% BSA) for 1 hour and incubated with radiolabelled heparin (~10 µg/ml) for 1 hour in the same buffer. Unlabelled heparin (6 mg/ml) is added for competition of binding. The membranes are washed (three 10 minutes washes in 10 mM Tris, pH 7.4). A Bas 2000 radioimaging system (Fuji) can be used for visualization of radioactivity.

Electron Microscopy

Suspensions of *P. aeruginosa* ($1.6 \times 10^6$ per sample) are incubated for 2 hours at 37° C. with different anti-microbial peptides at 50% of their required bactericidal concentration (50% lethal dose, LD$_{50}$). Peptides include the control LL-37 (0.6 µM) and varied concentrations of various heparin-binding peptides of the invention. Each sample is transferred onto poly L-lysine-coated Nylaflo® (GelmanSciences) nylon membranes. The membranes are fixed and processed for electron microscopy as described (Andersson et al. Eur. J. Biochem. 2004, 271:1219-1226). Electron micrographs of treated microbes are examined for morphological changes and perturbations such as breaks along cell membranes.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims should be construed to include all such embodiments and equivalent variations.

We claim:

1. A heparin-binding peptide consisting of an amino acid sequence selected from the group consisting of SEQ ID NO:1, SEQ ID NO:5, SEQ ID NO:8 and SEQ ID NO:37, wherein said heparin-binding peptide optionally comprises an amino-terminal protecting group or a carboxy-terminal protecting groups or both an amino-terminal protecting group and a carboxy-terminal protecting group.

2. A pharmaceutical composition comprising at least one peptide of claim 1 and a pharmaceutically-acceptable carrier.

3. A conjugate comprising a heparin-binding peptide according to claim 1 conjugated to at least one carrier molecule.

4. A conjugate according to claim 3, wherein said carrier molecule is selected from the group consisting of collagen, hyaluronic acid and agarose.

5. A conjugate according to claim 3, wherein said carrier molecule is further conjugated to a surgical sheet or mat.

6. The heparin binding peptide of claim 1 consisting of the amino acid sequence SEQ ID NO:1.

7. The heparin binding peptide of claim 1 consisting of the amino acid sequence SEQ ID NO:5.

8. The heparin binding peptide of claim 1 consisting of the amino acid sequence SEQ ID NO:8.

9. The heparin binding peptide of claim 1 consisting of the amino acid sequence SEQ ID NO:37.

10. The pharmaceutical composition according to claim 2, wherein the heparin binding peptide consists of the amino acid sequence SEQ ID NO:1.

11. The pharmaceutical composition according to claim 2, wherein the heparin binding peptide consists of the amino acid sequence SEQ ID NO:5.

12. The pharmaceutical composition according to claim 2, wherein the heparin binding peptide consists of the amino acid sequence SEQ ID NO:8.

13. The pharmaceutical composition according to claim 2, wherein the heparin binding peptide consists of the amino acid sequence SEQ ID NO:37.

14. The conjugate according to claim 3, wherein the heparin binding peptide consists of the amino acid sequence SEQ ID NO:1.

15. The conjugate according to claim 3, wherein the heparin binding peptide consists of the amino acid sequence SEQ ID NO:5.

16. The conjugate according to claim 3, wherein the heparin binding peptide consists of the amino acid sequence SEQ ID NO:8.

17. The conjugate according to claim 3, wherein the heparin binding peptide consists of the amino acid sequence SEQ ID NO:37.

* * * * *

SEQUENCE LISTING

<160> NUMBER OF SEQ ID NOS: 47

<210> SEQ ID NO 1
<211> LENGTH: 40
<212> TYPE: PRT

-continued

```
<213> ORGANISM: Artificial Sequence
<220> FEATURE:
<223> OTHER INFORMATION: Fragment

<400> SEQUENCE: 1

Ala Arg Lys Lys Ala Ala Lys Ala Ala Arg Lys Lys Ala Ala Lys Ala
 1               5                  10                  15

Ala Arg Lys Lys Ala Ala Lys Ala Ala Arg Lys Lys Ala Ala Lys Ala
                20                  25                  30

Val Leu Val Leu Val Leu Val Leu
            35                  40

<210> SEQ ID NO 2
<211> LENGTH: 8
<212> TYPE: PRT
<213> ORGANISM: Artificial Sequence
<220> FEATURE:
<223> OTHER INFORMATION: Fragment

<400> SEQUENCE: 2

Val Leu Val Leu Val Leu Val Leu
 1               5

<210> SEQ ID NO 3
<211> LENGTH: 8
<212> TYPE: PRT
<213> ORGANISM: Artificial Sequence
<220> FEATURE:
<223> OTHER INFORMATION: Fragment

<400> SEQUENCE: 3

Ile Leu Ile Leu Ile Leu Ile Leu
 1               5

<210> SEQ ID NO 4
<211> LENGTH: 8
<212> TYPE: PRT
<213> ORGANISM: Artificial Sequence
<220> FEATURE:
<223> OTHER INFORMATION: Fragment

<400> SEQUENCE: 4

Val Ile Val Ile Val Ile Val Ile
 1               5

<210> SEQ ID NO 5
<211> LENGTH: 32
<212> TYPE: PRT
<213> ORGANISM: Artificial Sequence
<220> FEATURE:
<223> OTHER INFORMATION: Fragment

<400> SEQUENCE: 5

Ala Arg Lys Lys Ala Ala Lys Ala Ala Arg Lys Lys Ala Ala Lys Ala
 1               5                  10                  15

Ala Arg Lys Lys Ala Ala Lys Ala Val Leu Val Leu Val Leu Val Leu
                20                  25                  30

<210> SEQ ID NO 6
<211> LENGTH: 36
<212> TYPE: PRT
<213> ORGANISM: Artificial Sequence
<220> FEATURE:
<223> OTHER INFORMATION: Fragment

<400> SEQUENCE: 6
```

```
Ala Lys Lys Ala Arg Ala Ala Lys Lys Ala Arg Ala Ala Lys Lys Ala
 1               5                  10                  15

Arg Ala Ala Lys Lys Ala Arg Ala Ala Lys Lys Ala Arg Ala Val Leu
             20                  25                  30

Val Leu Val Leu
         35

<210> SEQ ID NO 7
<211> LENGTH: 30
<212> TYPE: PRT
<213> ORGANISM: Artificial Sequence
<220> FEATURE:
<223> OTHER INFORMATION: Fragment

<400> SEQUENCE: 7

Ala Arg Lys Lys Ala Ala Lys Ala Ala Arg Lys Lys Ala Ala Lys Ala
 1               5                  10                  15

Ala Arg Lys Lys Ala Ala Lys Ala Val Leu Val Leu Val Leu
             20                  25                  30

<210> SEQ ID NO 8
<211> LENGTH: 34
<212> TYPE: PRT
<213> ORGANISM: Artificial Sequence
<220> FEATURE:
<223> OTHER INFORMATION: Fragment

<400> SEQUENCE: 8

Ala Arg Lys Lys Ala Ala Lys Ala Ala Arg Lys Lys Ala Ala Lys Ala
 1               5                  10                  15

Ala Arg Lys Lys Ala Ala Lys Ala Val Leu Val Leu Val Leu Val Leu
             20                  25                  30

Val Leu

<210> SEQ ID NO 9
<211> LENGTH: 24
<212> TYPE: PRT
<213> ORGANISM: Artificial Sequence
<220> FEATURE:
<223> OTHER INFORMATION: Fragment

<400> SEQUENCE: 9

Ala Arg Lys Lys Ala Ala Lys Ala Ala Arg Lys Lys Ala Ala Lys Ala
 1               5                  10                  15

Val Leu Val Leu Val Leu Val Leu
             20

<210> SEQ ID NO 10
<211> LENGTH: 16
<212> TYPE: PRT
<213> ORGANISM: Artificial Sequence
<220> FEATURE:
<223> OTHER INFORMATION: Fragment

<400> SEQUENCE: 10

Ala Arg Lys Lys Ala Ala Lys Ala Val Leu Val Leu Val Leu Val Leu
 1               5                  10                  15

<210> SEQ ID NO 11
<211> LENGTH: 32
<212> TYPE: PRT
<213> ORGANISM: Artificial Sequence
<220> FEATURE:
```

<223> OTHER INFORMATION: Fragment

<400> SEQUENCE: 11

Ala Arg Lys Lys Ala Ala Lys Ala Val Leu Val Leu Val Leu Val Leu
1               5                   10                  15

Ala Arg Lys Lys Ala Ala Lys Ala Ala Arg Lys Lys Ala Ala Lys Ala
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Fragment

<400> SEQUENCE: 12

Ala Arg Lys Lys Ala Ala Lys Ala Ala Arg Lys Lys Ala Ala Lys Ala
1               5                   10                  15

Ala Arg Lys Lys Ala Ala Lys Ala Ile Leu Ile Leu Ile Leu Ile Leu
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Fragment

<400> SEQUENCE: 13

Ala Arg Lys Lys Ala Ala Lys Ala Ala Arg Lys Lys Ala Ala Lys Ala
1               5                   10                  15

Ala Arg Lys Lys Ala Ala Lys Ala Val Ile Val Ile Val Ile Val Ile
            20                  25                  30

<210> SEQ ID NO 14
<211> LENGTH: 25
<212> TYPE: PRT
<213> ORGANISM: Artificial Sequence
<220> FEATURE:
<223> OTHER INFORMATION: Fragment

<400> SEQUENCE: 14

Val Leu Val Leu Ala Arg Lys Lys Ala Ala Lys Ala Pro Ala Arg Lys
1               5                   10                  15

Lys Ala Ala Lys Ala Val Leu Val Leu
            20                  25

<210> SEQ ID NO 15
<211> LENGTH: 25
<212> TYPE: PRT
<213> ORGANISM: Artificial Sequence
<220> FEATURE:
<223> OTHER INFORMATION: Fragment

<400> SEQUENCE: 15

Val Leu Val Leu Ala Arg Lys Lys Ala Ala Lys Ala Pro Ala Ala Ala
1               5                   10                  15

Ala Ala Ala Ala Ala Val Leu Val Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Fragment

<400> SEQUENCE: 16

```
Val Leu Val Leu Ala Arg Lys Lys Ala Ala Lys Ala Pro Ala Arg Lys
 1               5                   10                  15
Lys Ala Ala Lys Ala Asp Val Leu Val Leu
             20                  25
```

<210> SEQ ID NO 17
<211> LENGTH: 25
<212> TYPE: PRT
<213> ORGANISM: Artificial Sequence
<220> FEATURE:
<223> OTHER INFORMATION: Fragment

<400> SEQUENCE: 17

```
Leu Val Leu Ala Arg Lys Lys Ala Ala Lys Ala Pro Ala Ala Ala
 1               5                   10                  15
Ala Ala Ala Ala Asp Val Leu Val Leu
             20                  25
```

<210> SEQ ID NO 18
<211> LENGTH: 21
<212> TYPE: PRT
<213> ORGANISM: Artificial Sequence
<220> FEATURE:
<223> OTHER INFORMATION: Fragment

<400> SEQUENCE: 18

```
Val Leu Val Leu Ala Lys Lys Ala Arg Ala Pro Ala Lys Lys Ala Arg
 1               5                   10                  15
Ala Val Leu Val Leu
             20
```

<210> SEQ ID NO 19
<211> LENGTH: 21
<212> TYPE: PRT
<213> ORGANISM: Artificial Sequence
<220> FEATURE:
<223> OTHER INFORMATION: Fragment

<400> SEQUENCE: 19

```
Val Leu Val Leu Ala Lys Lys Ala Arg Ala Pro Ala Ala Ala Ala
 1               5                   10                  15
Ala Val Leu Val Leu
             20
```

<210> SEQ ID NO 20
<211> LENGTH: 22
<212> TYPE: PRT
<213> ORGANISM: Artificial Sequence
<220> FEATURE:
<223> OTHER INFORMATION: Fragment

<400> SEQUENCE: 20

```
Val Leu Val Leu Ala Lys Lys Ala Arg Ala Pro Ala Lys Lys Ala Arg
 1               5                   10                  15
Ala Asp Val Leu Val Leu
             20
```

<210> SEQ ID NO 21
<211> LENGTH: 22
<212> TYPE: PRT

```
<213> ORGANISM: Artificial Sequence
<220> FEATURE:
<223> OTHER INFORMATION: Fragment

<400> SEQUENCE: 21

Val Leu Val Leu Ala Lys Lys Ala Arg Ala Pro Ala Ala Ala Ala
1               5                   10                  15

Ala Asp Val Leu Val Leu
            20

<210> SEQ ID NO 22
<211> LENGTH: 14
<212> TYPE: PRT
<213> ORGANISM: Artificial Sequence
<220> FEATURE:
<223> OTHER INFORMATION: Fragment

<400> SEQUENCE: 22

Val Leu Val Leu Ala Arg Lys Lys Ala Ala Lys Ala Cys Ala
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Fragment

<400> SEQUENCE: 23

Val Leu Val Leu Ala Arg Lys Lys Ala Ala Lys Ala Cys Ala Asp Ala
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Fragment

<400> SEQUENCE: 24

Val Leu Val Leu Ala Lys Lys Ala Arg Ala Cys Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Fragment

<400> SEQUENCE: 25

Val Leu Val Leu Ala Lys Lys Ala Arg Ala Cys Ala Asp Ala
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Fragment

<400> SEQUENCE: 26

Cys Ala Asp Ala
1

<210> SEQ ID NO 27
```

```
<211> LENGTH: 4
<212> TYPE: PRT
<213> ORGANISM: Artificial Sequence
<220> FEATURE:
<223> OTHER INFORMATION: Fragment

<400> SEQUENCE: 27

Val Leu Val Leu
 1

<210> SEQ ID NO 28
<211> LENGTH: 6
<212> TYPE: PRT
<213> ORGANISM: Artificial Sequence
<220> FEATURE:
<223> OTHER INFORMATION: Fragment

<400> SEQUENCE: 28

Val Leu Val Leu Val Leu
 1               5

<210> SEQ ID NO 29
<211> LENGTH: 8
<212> TYPE: PRT
<213> ORGANISM: Artificial Sequence
<220> FEATURE:
<223> OTHER INFORMATION: Fragment

<400> SEQUENCE: 29

Ala Arg Lys Lys Ala Ala Lys Ala
 1               5

<210> SEQ ID NO 30
<211> LENGTH: 32
<212> TYPE: PRT
<213> ORGANISM: Artificial Sequence
<220> FEATURE:
<223> OTHER INFORMATION: Fragment

<400> SEQUENCE: 30

Ala Arg Lys Lys Ala Ala Lys Ala Ala Ala Ala Ala Ala Ala Ala Ala
 1               5                  10                  15

Ala Ala Ala Ala Ala Ala Ala Ala Arg Lys Lys Ala Ala Lys Ala
             20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Fragment

<400> SEQUENCE: 31

Ala Arg Lys Lys Ala Ala Lys Ala Ala Arg Lys Lys Ala Ala Lys Ala
 1               5                  10                  15

Ala Arg Lys Lys Ala Ala Lys Ala Ala Arg Lys Lys Ala Ala Lys Ala
             20                  25                  30

<210> SEQ ID NO 32
<211> LENGTH: 36
<212> TYPE: PRT
<213> ORGANISM: Artificial Sequence
<220> FEATURE:
<223> OTHER INFORMATION: Fragment

<400> SEQUENCE: 32
```

```
Ala Lys Lys Ala Arg Ala Ala Lys Lys Ala Arg Ala Ala Lys Lys Ala
 1               5                   10                  15

Arg Ala Ala Lys Lys Ala Arg Ala Ala Lys Lys Ala Arg Ala Ala Lys
                20                  25                  30

Lys Ala Arg Ala
         35
```

<210> SEQ ID NO 33
<211> LENGTH: 32
<212> TYPE: PRT
<213> ORGANISM: Artificial Sequence
<220> FEATURE:
<223> OTHER INFORMATION: Fragment

<400> SEQUENCE: 33

```
Ala Arg Lys Lys Ala Ala Lys Ala Ala Arg Lys Lys Ala Ala Lys Ala
 1               5                   10                  15

Ala Arg Lys Lys Ala Ala Lys Ala Ala Arg Lys Lys Cys Ala Lys Ala
                20                  25                  30
```

<210> SEQ ID NO 34
<211> LENGTH: 34
<212> TYPE: PRT
<213> ORGANISM: Artificial Sequence
<220> FEATURE:
<223> OTHER INFORMATION: Fragment

<400> SEQUENCE: 34

```
Cys Ala Arg Lys Lys Ala Ala Lys Ala Ala Arg Lys Lys Ala Ala Lys
 1               5                   10                  15

Ala Ala Arg Lys Lys Ala Ala Lys Ala Ala Arg Lys Lys Ala Ala Lys
                20                  25                  30

Ala Cys
```

<210> SEQ ID NO 35
<211> LENGTH: 4
<212> TYPE: PRT
<213> ORGANISM: Artificial Sequence
<220> FEATURE:
<223> OTHER INFORMATION: Fragment

<400> SEQUENCE: 35

```
Ile Leu Ile Leu
 1
```

<210> SEQ ID NO 36
<211> LENGTH: 6
<212> TYPE: PRT
<213> ORGANISM: Artificial Sequence
<220> FEATURE:
<223> OTHER INFORMATION: Fragment

<400> SEQUENCE: 36

```
Ile Leu Ile Leu Ile Leu
 1               5
```

<210> SEQ ID NO 37
<211> LENGTH: 36
<212> TYPE: PRT
<213> ORGANISM: Artificial Sequence
<220> FEATURE:
<223> OTHER INFORMATION: Fragment

<400> SEQUENCE: 37

```
Ala Arg Lys Lys Ala Ala Lys Ala Ala Arg Lys Lys Ala Ala Lys Ala
 1               5                   10                  15

Ala Arg Lys Lys Ala Ala Lys Ala Val Leu Val Leu Val Leu Val Leu
                20                  25                  30

Val Leu Val Leu
        35
```

<210> SEQ ID NO 38
<211> LENGTH: 36
<212> TYPE: PRT
<213> ORGANISM: Artificial Sequence
<220> FEATURE:
<223> OTHER INFORMATION: Fragment

<400> SEQUENCE: 38

```
Val Leu Val Leu Ala Arg Lys Lys Ala Ala Lys Ala Ala Arg Lys Lys
 1               5                   10                  15

Ala Ala Lys Ala Ala Arg Lys Lys Ala Ala Lys Ala Ala Arg Lys Lys
                20                  25                  30

Cys Ala Lys Ala
        35
```

<210> SEQ ID NO 39
<211> LENGTH: 4
<212> TYPE: PRT
<213> ORGANISM: Artificial Sequence
<220> FEATURE:
<223> OTHER INFORMATION: Fragment

<400> SEQUENCE: 39

```
Val Ile Val Ile
 1
```

<210> SEQ ID NO 40
<211> LENGTH: 6
<212> TYPE: PRT
<213> ORGANISM: Artificial Sequence
<220> FEATURE:
<223> OTHER INFORMATION: Fragment

<400> SEQUENCE: 40

```
Val Ile Val Ile Val Ile
 1               5
```

<210> SEQ ID NO 41
<211> LENGTH: 6
<212> TYPE: PRT
<213> ORGANISM: Artificial Sequence
<220> FEATURE:
<223> OTHER INFORMATION: Fragment

<400> SEQUENCE: 41

```
Ala Lys Lys Ala Arg Ala
 1               5
```

<210> SEQ ID NO 42
<211> LENGTH: 8
<212> TYPE: PRT
<213> ORGANISM: Artificial Sequence
<220> FEATURE:
<223> OTHER INFORMATION: Fragment

<400> SEQUENCE: 42

```
Leu Leu Leu Leu Leu Leu Leu Leu
 1               5
```

<210> SEQ ID NO 43
<211> LENGTH: 8
<212> TYPE: PRT
<213> ORGANISM: Artificial Sequence
<220> FEATURE:
<223> OTHER INFORMATION: Fragment

<400> SEQUENCE: 43

Val Phe Val Phe Val Phe Val Phe
1               5

<210> SEQ ID NO 44
<211> LENGTH: 12
<212> TYPE: PRT
<213> ORGANISM: Artificial Sequence
<220> FEATURE:
<223> OTHER INFORMATION: Fragment

<400> SEQUENCE: 44

Val Leu Val Leu Val Leu Val Leu Val Leu Val Leu
1               5                   10

<210> SEQ ID NO 45
<211> LENGTH: 32
<212> TYPE: PRT
<213> ORGANISM: Artificial Sequence
<220> FEATURE:
<223> OTHER INFORMATION: Fragment

<400> SEQUENCE: 45

Ala Arg Lys Lys Ala Ala Lys Ala Ala Arg Lys Lys Ala Ala Lys Ala
1               5                   10                  15

Ala Arg Lys Lys Ala Ala Lys Ala Leu Leu Leu Leu Leu Leu Leu Leu
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Fragment

<400> SEQUENCE: 46

Ala Arg Lys Lys Ala Ala Lys Ala Ala Arg Lys Lys Ala Ala Lys Ala
1               5                   10                  15

Ala Arg Lys Lys Ala Ala Lys Ala Val Phe Val Phe Val Phe Val Phe
            20                  25                  30

<210> SEQ ID NO 47
<211> LENGTH: 40
<212> TYPE: PRT
<213> ORGANISM: Artificial Sequence
<220> FEATURE:
<223> OTHER INFORMATION: Fragment

<400> SEQUENCE: 47

Ala Arg Lys Lys Ala Ala Lys Ala Ala Arg Lys Lys Ala Ala Lys Ala
1               5                   10                  15

Val Leu Val Leu Val Leu Val Leu Ala Arg Lys Lys Ala Ala Lys Ala
            20                  25                  30

Ala Arg Lys Lys Ala Ala Lys Ala
            35                  40